United States Patent
Lockledge et al.

(10) Patent No.: US 8,691,096 B2
(45) Date of Patent: Apr. 8, 2014

(54) OIL FILTERS CONTAINING STRONG BASE AND METHODS OF THEIR USE

(71) Applicant: Luteck, LLC, Wilmington, DE (US)

(72) Inventors: Scott P. Lockledge, West Chester, PA (US); Darrell W. Brownawell, Black Butte Ranch, OR (US)

(73) Assignee: Lutek, LLC, Wilmington, DE (US)

( * ) Notice: Subject to any disclaimer, the term of this patent is extended or adjusted under 35 U.S.C. 154(b) by 0 days.

(21) Appl. No.: 13/677,857

(22) Filed: Nov. 15, 2012

(65) Prior Publication Data

US 2013/0068694 A1 Mar. 21, 2013

Related U.S. Application Data

(63) Continuation of application No. 13/417,544, filed on Mar. 12, 2012, now abandoned, which is a continuation of application No. 12/264,792, filed on Nov. 4, 2008, now abandoned.

(60) Provisional application No. 61/025,639, filed on Feb. 1, 2008.

(51) Int. Cl.
*B01D 37/02* (2006.01)
*B01D 37/03* (2006.01)

(52) U.S. Cl.
USPC ...... 210/665; 210/777; 210/724; 210/167.02; 210/167.08; 210/416.5; 210/502.1; 210/504; 184/6.24; 123/196 A

(58) Field of Classification Search
USPC ........ 123/1 R, 196 R, 196 A; 184/6.24, 6.21; 210/665, 777, 724, 167.02, 167.08, 210/416.5, 502.1, 504
See application file for complete search history.

(56) References Cited

U.S. PATENT DOCUMENTS

| | | | |
|---|---|---|---|
| 2,316,080 A | 4/1943 | Loane et al. |
| 2,617,049 A | 11/1952 | Asseff et al. |
| 2,647,889 A | 8/1953 | Watson et al. |
| 2,835,688 A | 5/1958 | LeSuer |

(Continued)

FOREIGN PATENT DOCUMENTS

| | | |
|---|---|---|
| EP | 0331516 | 6/1989 |
| EP | 0416907 | 3/1991 |

(Continued)

OTHER PUBLICATIONS

"CFF Fibrillated Fiber", Sterling Fibers, Sterling Fibers Incorporated, © 1997, 6 pages.

(Continued)

*Primary Examiner* — David C Mellon
(74) *Attorney, Agent, or Firm* — Baker & Hostetler LLP

(57) ABSTRACT

Novel filter elements for sequestering acids from oil or fuel, the strong base flocs that comprise the filter elements, and methods of their preparation and use are disclosed. The filter elements comprise a mechanically linked interlocking fiber matrix interspersed with strong base particle flocs wherein the strong base particles constitute at least 30% by weight of the filter element. Certain filter elements may be useful for sequestering acids or neutralized acids in certain oils or fuels, for example, the acids originating in the combustion and lubrication system of an internal combustion engine or those contained in oils in an oil circulation system. Other filter elements may be useful for reducing oxidation of an oil.

6 Claims, 9 Drawing Sheets

(56) References Cited

U.S. PATENT DOCUMENTS

| | | | |
|---|---|---|---|
| 3,172,892 | A | 3/1965 | Le Suer et al. |
| 3,796,778 | A | 3/1974 | Gallacher |
| 4,212,746 | A | 7/1980 | Tholema et al. |
| 4,664,683 | A | 5/1987 | Degen et al. |
| 4,717,552 | A | 1/1988 | Carnell et al. |
| 4,828,698 | A | 5/1989 | Jewell et al. |
| 4,861,566 | A | 8/1989 | Denny |
| 4,865,826 | A | 9/1989 | Carnell et al. |
| 4,888,157 | A | 12/1989 | Carnell et al. |
| 4,894,210 | A | 1/1990 | Denny et al. |
| 4,906,389 | A | 3/1990 | Brownawell et al. |
| 4,946,660 | A | 8/1990 | Denny et al. |
| 4,977,871 | A | 12/1990 | Brownawell et al. |
| 4,978,439 | A | 12/1990 | Carnell et al. |
| 4,983,365 | A | 1/1991 | Denny et al. |
| 4,997,546 | A | 3/1991 | Shaub et al. |
| 5,019,311 | A * | 5/1991 | Koslow .................. 264/122 |
| 5,042,617 | A | 8/1991 | Brownawell et al. |
| 5,068,044 | A | 11/1991 | Brownawell et al. |
| 5,069,799 | A | 12/1991 | Brownawell et al. |
| 5,112,482 | A | 5/1992 | Shaub et al. |
| 5,147,722 | A | 9/1992 | Koslow |
| 5,164,101 | A | 11/1992 | Brownawell et al. |
| 5,182,018 | A | 1/1993 | Langston |
| 5,189,092 | A | 2/1993 | Koslow |
| 5,225,081 | A | 7/1993 | Brownawell |
| 5,249,948 | A | 10/1993 | Koslow |
| 5,330,666 | A | 7/1994 | Habeeb |
| 5,331,037 | A | 7/1994 | Koslow |
| 5,346,619 | A | 9/1994 | Funkenbusch |
| 5,459,074 | A | 10/1995 | Muoni |
| 5,478,463 | A | 12/1995 | Brownawell et al. |
| 5,591,330 | A | 1/1997 | Lefebvre |
| 5,759,394 | A | 6/1998 | Rohrbach et al. |
| 5,792,513 | A | 8/1998 | Koslow et al. |
| 5,853,681 | A | 12/1998 | Denny et al. |
| 5,882,517 | A | 3/1999 | Chen et al. |
| 5,897,845 | A | 4/1999 | Denny et al. |
| 5,922,803 | A | 7/1999 | Koslow et al. |
| 5,928,588 | A | 7/1999 | Chen et al. |
| 6,007,706 | A | 12/1999 | Carnell et al. |
| 6,077,588 | A | 6/2000 | Koslow et al. |
| 6,103,116 | A | 8/2000 | Koslow et al. |
| 6,127,036 | A | 10/2000 | Xue et al. |
| 6,139,605 | A | 10/2000 | Carnell et al. |
| 6,221,241 | B1 | 4/2001 | Carnell et al. |
| 6,355,330 | B1 | 3/2002 | Koslow et al. |
| 6,379,564 | B1 | 4/2002 | Rohrbach et al. |
| 6,395,190 | B1 | 5/2002 | Koslow et al. |
| 6,482,326 | B2 | 11/2002 | Munson et al. |
| 6,485,813 | B1 | 11/2002 | Koslow |
| 6,505,597 | B2 | 1/2003 | Zulauf et al. |
| 6,537,453 | B2 | 3/2003 | Beard et al. |
| 6,550,622 | B2 | 4/2003 | Koslow |
| 6,623,636 | B2 | 9/2003 | Rohrbach et al. |
| 6,630,016 | B2 | 10/2003 | Koslow |
| 6,703,071 | B2 | 3/2004 | Koslow |
| 6,719,869 | B2 | 4/2004 | Koslow |
| 6,770,204 | B1 | 8/2004 | Koslow |
| 7,250,126 | B2 | 7/2007 | Haberkamp et al. |
| 7,410,572 | B2 | 8/2008 | Beard et al. |
| 7,520,371 | B2 | 4/2009 | Lockledge et al. |
| 7,913,858 | B2 | 3/2011 | Haberkamp et al. |
| 2002/0014447 | A1 | 2/2002 | Rohrbach et al. |
| 2002/0028166 | A1 | 3/2002 | Hendricks et al. |
| 2002/0053328 | A1 | 5/2002 | Pudelski et al. |
| 2002/0195384 | A1 | 12/2002 | Rohrbach et al. |
| 2003/0089092 | A1 | 5/2003 | Bause et al. |
| 2003/0111398 | A1 | 6/2003 | Eilers et al. |
| 2004/0178142 | A1 | 9/2004 | Koslow |
| 2005/0040092 | A1 | 2/2005 | Eilers et al. |
| 2006/0000760 | A1 | 1/2006 | Beard et al. |
| 2006/0032814 | A1 | 2/2006 | Haberkamp et al. |
| 2006/0260874 | A1 | 11/2006 | Lockledge et al. |
| 2006/0261004 | A1 * | 11/2006 | Lockledge et al. ........ 210/502.1 |
| 2007/0040559 | A1 | 2/2007 | Klun |

FOREIGN PATENT DOCUMENTS

| | | |
|---|---|---|
| EP | 1167497 | 1/2002 |
| WO | WO 01/05583 | 1/2001 |
| WO | WO 01/92005 | 12/2001 |
| WO | WO 02/32548 | 4/2002 |
| WO | WO 02/083265 | 10/2002 |
| WO | WO 2004/065530 | 8/2004 |
| WO | WO 2006/066767 | 6/2006 |
| WO | WO 2006/066768 | 6/2006 |
| WO | WO 2006/127652 | 5/2007 |
| WO | WO 2009/099882 | 12/2009 |

OTHER PUBLICATIONS

"CFF Fibrillated Fiber: High Periormance Nonwoven Filtration Media", Sterling Fibers, Sterling Fibers Incorporated, © 1997, 4 pages.

"Guidelines for Processing CFF Fibrillated Fibers: For Use in Wet-Laid Specialty Papers, Filtration Media and Nonwovens", Sterling Fibers, 2004, 1-20.

Asselman, et al., "The Flocculation Mechanism of Microparticulate Retention Aid Systems", Journal of Pulp and Paper Science, Aug. 2001, vol. 27(8), 273-278.

Baum, et al., "Papermaking additives", Encyclopedia of Chemical Technology, 1978, 16, 803-805.

Clague et al., "A comparison of Diesel Engine Soot With Carbon Black", Carbon, Jan. 1999, 37(10), 1553-1565.

European Patent Application No. EP 09708905: Supplementary European Search Report dated Oct. 27, 2011, 12 pages.

Mann, "Fluid Catalytic Cracking: Some Recent Developments in Catalyst Particle Design and Unit Hardware", Catalysis Today, Dec. 31, 1993, 18(4), 509-528.

Mathis et al., "Influence of Diesel Engine Combustion Parameters on Primary Soot Particle Diameter", Environmental Science and Technology, Mar. 15, 2005, 39(6), 1887-1892.

McNeal, et al.,"Understanding nanoparticle/microparticle performance through visualization of conformational changes of a retention aid at the nanoscale level", 2006, XP002660028, Database Accession No. E20070110343211.

Mirrezaei-Roudaki, "Applications of Visualized Porosimetry for Pore Structure Characterisation of Adsorbents and Catalysts", The 1994 ICHEME Research Event, London, England, Jan. 5 and 6, 1994, 565-567.

Moss et al., "Flocculation: Theory & Application", Mine and Quarry Journal, May 2, 1978, 1-9.

Nasser, et al., "The effect of polyacrylamide charge density and molecular weight on the flocculation and sedimentation behaviour of kaolinite suspensions", Separation and Purification Technology, Elsevier Science, Apr. 19, 2006, 52(2), 241-252.

Schetelich et al., "The Control of Piston Crown Land Deposits in Diesel Engine Through Oil Formulation", Soc. Automat. Eng. Tech. Pub. Ser., Paper No. 861517, Oct. 1, 1986, 74-82.

Spikes, "The history and mechanisms of ZDDP", Tribology Letters, Oct. 2004, 17(3), 469-489.

Webb et al., "An Introduction to the Physical Characterization of Materials by Mercury Intrusion Porosimetry with Emphasis on Reduction and Presentation of Experimental Data", Micromeritics Instrument Corporation, Norcross, GA, Jan. 2001, 1-22.

Webb et al., "Analytical methods in fine particle technology", Micrometrics Instrument Corp., 1997, 172-173.

Won et al., "Effect of Temperature on Carbon-Black Agglomerates in Hydrocarbon Liquid with Adsorbed Dispersant", Langmuir, Feb. 2005, 21(3), 924-932.

\* cited by examiner

Exemplary Process to Make a Strong Base Filter Element

OIL FILTERS CONTAINING STRONG BASE AND METHODS OF THEIR USE

CROSS REFERENCE TO RELATED APPLICATION

This application is a Continuation of U.S. patent application Ser. No. 13/417,544 filed Mar. 12, 2012, now abandoned, which is a Continuation of U.S. patent application Ser. No. 12/264,792 filed Nov. 4, 2008, now abandoned, which claims benefit to U.S. Provisional Application No. 61/025,639 filed Feb. 1, 2008, now expired.

FIELD OF THE INVENTION

The present invention relates to filter elements useful for sequestering combustion acids in solid base-containing oil filters, where the filter elements include strong base flocs, and methods of their preparation and their use.

BACKGROUND OF THE INVENTION

Optimal functioning of an internal combustion engine (e.g., a diesel engine) requires that combustion acids, e.g. carboxylic, nitric, nitrous, sulfuric and sulfurous acid, with or without alkyl groups, be neutralized where or near where they first contact the lubricant, i.e., near the piston. In the absence of this acid neutralization, the engine corrodes, the lubricant gels, the viscosity rapidly increases, and engine deposits form. These actions result in increased oil consumption and engine wear.

Traditionally, metal-containing detergents, such as barium, calcium, or magnesium overbased sulfonates or phenates, neutralize combustion acids in lubricant systems. (See U.S. Pat. Nos. 2,316,080; 2,617,049; 2,647,889; and 2,835,688). In lubricants where metal detergents are absent, polyethyleneamine based dispersants or other ashless dispersants neutralize combustion acids. (See U.S. Pat. No. 3,172,892). At the loadings needed to effectively neutralize combustion acids in internal combustion engine lubricants, ashless detergents are less cost effective than ash-containing detergents. As a consequence, ashless dispersants are relegated mainly to the purpose of maintaining engine cleanliness, where their cost is less of an issue.

Well formulated lubricants containing metal detergents are very effective in neutralizing combustion acids. This neutralization helps to prevent corrosion and reduce piston deposits. At high detergent concentrations, however, metal detergents begin to deposit on pistons offsetting desired detergency improvements. For example, the deposits on some pistons contain up to 34% calcium and magnesium derived from the detergent. See A. Schetelich et. al., "The Control of Piston Crown Land Deposits in Diesel Engines Through Oil Formulation," Soc. Automat. Eng. Tech., Pub. Ser. 861517 (1986).

U.S. Pat. Nos. 4,906,389; 5,068,044; 5,069,799; and 5,164,101 disclose the use of a strong base located in the oil filter. Combustion acids passing by the piston are thought to be neutralized by a weak base additive in the dispersant. Dispersant contained in the oil carries the combustion acid to the strong base in the filter. In the oil filter, the combustion acid transfers from the weak base dispersant to the strong base and is sequestered. The dispersant remains in the lubricant and passes back to the piston where it may neutralize additional combustion acid. At the same time, ash-containing detergent in the oil is neutralizing combustion acid and transporting it to the filter where it may be sequestered. To the degree that combustion acid is sequestered in the oil filter, certain advantages may arise. First, additional combustion acid may be neutralized without increasing the concentration of the ash-containing detergent. Second, the interval between oil drains may be increased. Third, the concentration of the ash-containing detergent can be reduced without decreasing the amount of combustion acid that can be neutralized, or the user may choose some combination of the above to fit his or her particular requirements. A variety of strong bases that can effectively be immobilized in the oil filter and that are effective neutralizing agents include barium oxide, calcium carbonate, calcium hydroxide, calcium oxide, magnesium carbonate, magnesium hydroxide, magnesium oxide, sodium aluminate, sodium carbonate, sodium hydroxide, zinc oxide, or mixtures thereof.

Like U.S. Pat. No. 5,164,101, PCT publications WO2006/066767 and WO2006/066768 each disclose aspects of a lubricant containing a minor amount of certain weak bases (oil-soluble succinimides) in combination with an immobilized base to remove combustion acids from circulating oil in an internal combustion engine, in particular those engines with exhaust gas recirculation systems (EGR) wherein the EGR does not have a chemical filter. The two publications disclose improved performance when particular molecular weight succinimides are employed in contrast to the earlier issued U.S. Pat. No. 5,164,101.

Other U.S. Patents and U.S. Patent Applications have disclosed the optimization of different aspects of a strong base oil filter. For example, U.S. Pat. No. 6,537,453 B2 discloses a specific design of an oil filter using one of three acid-neutralizing compounds; i.e. crushed limestone, calcium carbonate or magnesium carbonate.

U.S. Patent Application 2006/0000760 A1 teaches a specific oil filter design containing a venturi device to control oil pressure in order to direct oil flow to the acid-neutralizing compound in the oil filter.

U.S. Patent Application 2004/0178142 discloses an integrated paper having active particles immobilized therein wherein the paper comprises a plurality of fibrillated fibers having an average diameter of less than about 1000 nm and the pore size of the paper is less than or equal to about 2 μm. A list of active agents that may be immobilized includes magnesium oxide. The application further discloses lubricant oil filtration devices comprising the integrated paper in contact with lubricant oil.

U.S. Pat. No. 7,250,126 B2 discloses a process for incorporating a strong base into paper that is then used as a filter media. This application further highlights the value of choosing a strong base that has low molecular weight and divalent chemistry in order to minimize the grams of strong base required. Additionally, U.S. Pat. No. 7,250,126 B2 discloses acid-neutralizing filter media for a liquid filter in a liquid filtration system and further discloses that strong base particle diameters of greater than 10 microns are known to cause increased engine wear in engine lubrication systems. U.S. Pat. No. 7,250,126 B2 also discloses the use of adhesive binders to form strong base agglomerates in strong base filter elements.

U.S. Patent Publication 2006/0261004 A1 discloses that the capacity of a strong base oil filter is directly related to the surface area associated with pores of a defined minimum diameter.

U.S. Patent Publication 2006/0260874 A1 discloses that the use of a strong base filter to replace detergent in the lubricant may allow reductions or elimination of detergents in the oil that in turn may result in modulation of piston deposit levels, improved emission treatment equipment efficiency, or improved performance of the ubiquitous anti-wear oil additive, zinc dialkyldithiophosphate (ZnDDP).

However, these disclosures have not led to commercialization of an oil filter containing a strong base. Strong base migration from the filter to the lubricant remains an issue. Attempts to limit base migration (and related excess engine wear) have led to reduction in neutralization capacity of the strong base through, for example, reduction in reactive surface area. There remains a long felt need to achieve combustion acid neutralization without the need for high levels of ash-containing detergents in the lubricant and/or buildup of detergent-related piston deposits. It is an object of this invention to provide a commercially viable strong base-containing oil filter that may achieve combustion acid neutralization without the need for high levels of ash-containing detergents in the lubricant and/or buildup of detergent-related piston deposits.

New and better filter elements that, in use, can sequester acidic compounds in non-aqueous liquids and gaseous fluids are needed. In lubricating oils for internal combustion engines, sequestration may extend the life and usefulness of detergents in the fluid and extend intervals between oil drains. Further, other types of oxidation are inherent in systems where oxygen is present. These oxidations generate organic acids and the rates of these processes are acid-catalyzed. Once formed, these organic acids are not usually neutralized by dispersants or detergents and increased levels of these acids lead to even higher rates of their generation. Their rates of formation may be inhibited by reducing the levels of these acids through sequestering and/or neutralizing of acids in the strong base matrix, which may, in turn, extend the useful life of the fluid. If anti-wear agents in the fluid are degraded by acids, then passing fluids through a strong base filter element matrix may extend the useful life of the anti-wear agent. If anti-oxidants in a fluid are degraded by peroxides, then the sequestering of acids in a strong base matrix, which results in lowered oxidation rates, may extend the useful life of the fluid. The present invention is directed to these and other important ends.

SUMMARY OF THE INVENTION

Accordingly, the invention is directed, in part, to filter elements useful for sequestering combustion acid in solid base-containing oil filters, where the filter elements include strong base flocs, and methods of their preparation and their use.

The present invention is directed, in part, to filter elements for sequestering acids from oil or fuel, comprising:
  a matrix formed of mechanically-interlocking structural fibers and interstitial spaces;
  strong base particles within the matrix for sequestering acids from oil or fuel, the strong base particles having an average particle size less than the average cross-section of the interstitial spaces; and
  a high molecular weight flocculating agent to retain a strong base particle floc formed within the matrix;
  wherein:
  1) the smallest unit dimension of the strong base particle floc formed is greater than the average cross-section of the interstitial spaces;
  2) the strong base particles are substantially unattached to the mechanically-interlocked fibers and are physically bound within the matrix;
  3) there is substantially no latex chemically binding the strong base particles to the matrix; and
  4) the strong base particles constitute at least 30% by weight of the filter element.

The invention is also directed, in part, to methods for preparing filter elements for sequestering acids or neutralized acids in at least one oil, comprising:
  slurrying strong base particles in water, water-miscible solvent, or a combination thereof;
  adding a high molecular weight flocculating agent to floc the strong base particles;
  adding structural fibers, or structural fiber portions, or small diameter fibers, or small diameter fiber portions, or any combination thereof, to the slurry to form a fiber matrix interspersed with the floc of strong base particles;
  contacting the fiber matrix with a backing sheet material;
  substantially removing the water, water-miscible solvent, or combination thereof; and
  depositing the fiber matrix onto the backing sheet material.

Certain embodiments of the invention are directed to methods for sequestering acid from oil containing acids or neutralized acids in an oil circulation system, comprising:
  contacting oil in the oil circulation system with a filter element of the type described herein, where the filter element causing at least a portion of the acids to remain with the strong base particles within the filter element. Also, the strong-base-containing filter element preferably has a total surface area, as measured by Hg intrusion porosimetry, of at least 10 $m^2$/gram. In certain of these embodiments, the oil circulation system may be found in a combustion and lubrication system of an internal combustion engine. In other embodiments, the acids sequestered by the filter element of the invention originate in the combustion and/or lubrication system of an internal combustion engine.

Certain other aspects of the invention are directed to methods of reducing oxidation of an oil, comprising contacting the oil with a filter element of the type described herein so as to sequester acids at a rate such that oxidation of the oil is decreased by at least about 20% relative to the rate of oxidation in an oil in contact with a non-base containing filter element as is described immediately above and throughout the application.

The invention is also directed, in part, to strong base flocs comprising:
  strong base particles containing magnesium oxide or zinc oxide or combination thereof and having an average particle size of about 0.1 to about 10 microns; and
  a high molecular weight flocculating agent;
  wherein:
    the floc formed from contacting of the flocculating agent and the strong base particles has an average cross-section distance of greater than about 10 microns; and
    the strong base particles in the floc retain at least about 40% of their intrinsic surface area as measured by a mercury intrusion porosimetry.

DETAILED DESCRIPTION OF ILLUSTRATIVE EMBODIMENTS

Figure 1:
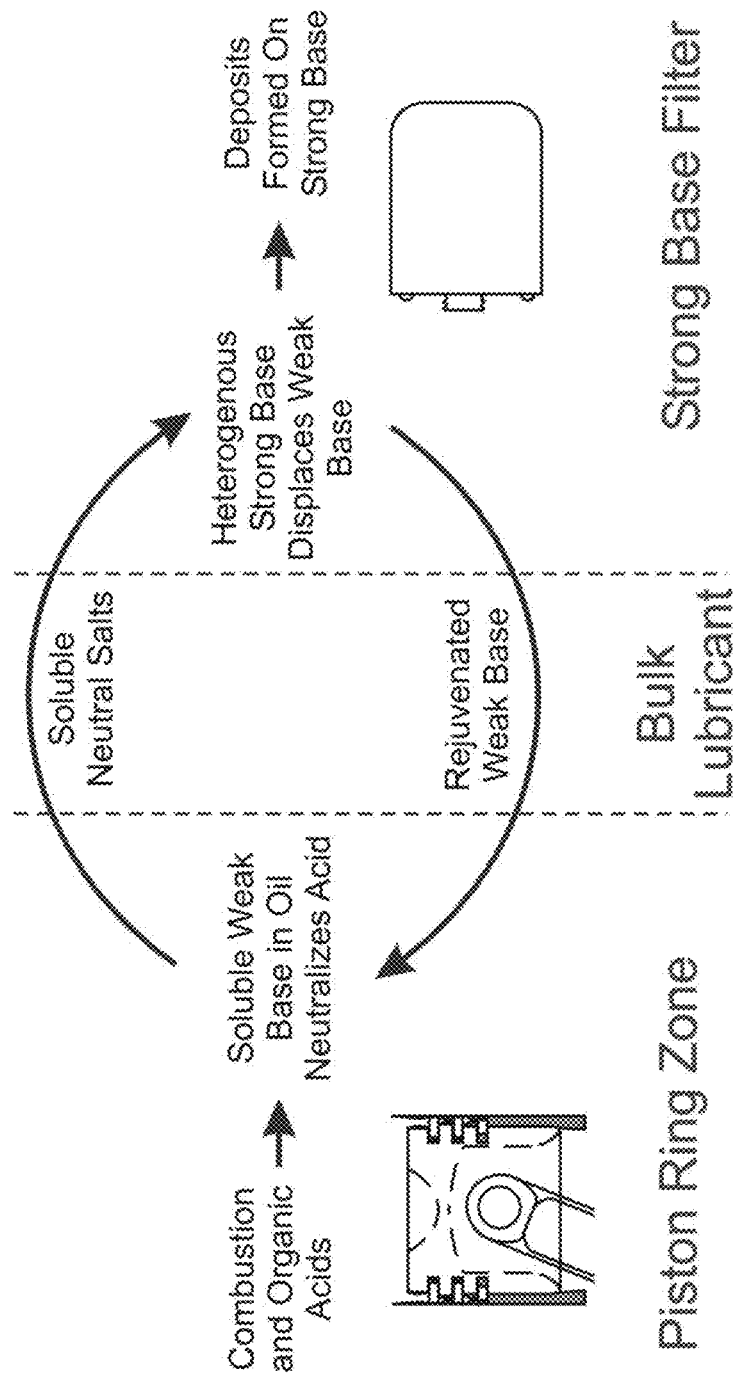
FIG. 1 pictorially represents a schematic of the transfer of combustion and/or organic acids to the filter's strong base from a weaker base, such as a detergent or dispersant.

The present invention is generally directed to filter elements for sequestering acids from oil, fluids, or fuel, the flocs that make up these filter elements, and methods of their use.

The present invention may be more readily understood by reference to the following detailed description of illustrative and preferred embodiments and the accompanying figures that form a part of this disclosure, and are not to be construed as limiting the appended claims. The invention claimed or disclosed herein is not limited to the specific devices, methods, conditions or parameters described and/or shown herein, and the terminology used herein is for the purpose of describing particular embodiments by way of example only. Neither is intended to limit the claimed invention. Also, as used in the specification including the appended claims, the singular forms "a", "an", and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about", it will be understood that the particular value forms another embodiment. When ranges are used herein, all combinations and subcombinations of ranges and specific embodiments therein are intended to be included.

The present invention comprises a superior acid sequestering filter medium and a method to make it. Generally the method involves the use of high molecular weight flocculants and/or microparticle retention aid systems in a wet-lay process to form strong base flocs. The filter elements are formed substantially without the use of adhesive latex binders that reduce surface area. Fibers included in the process retain these flocs in a fiber matrix via physical/mechanical retention. The flocs are not substantially attached to the fibers, but are restrained by an entangled web. This methodology results in a semi-continuous phase of magnesium oxide intermingled with fibers and is capable of filtering solid particulates as well as chemical sequestration of acid.

One advantage of this approach is that higher strong base particle loadings may be achieved in a filter matrix (since one is not limited by fiber surface area to which the strong base is attached) and higher intrinsic active strong base surface area may be retained (since adhesive binders that blind intrinsic active surface area are not used). These higher loadings and intrinsic active surfaces areas lead to higher total acid sequestration capacity and faster acid removal.

Fibrillated fibers are used in an exemplary embodiment to create a web or network to restrain large flocs. Also, a high percentage of MgO is retained in the filter element or paper, i.e. less MgO is lost to the effluent water, which reduces disposal problems and cost.

As employed above and throughout the disclosure, the following terms, unless otherwise indicated, shall be understood to have the following meanings.

As used herein, the term "chemical filter" or "chemically active filter" or "strong base filter" means a filter employing a strong base material that is capable of displacing a weak base from a combustion acid-weak base complex and/or is capable or neutralizing weak acids in the fluids that come into contact with the strong base material. Chemical filters and chemically active filters in accordance with the present invention may contain physically active filtration media in addition to the strong base material. They may also contain one or more inactive filters or filter members. The chemical filters of the present invention may also contain mixed filtration media made up of two or more different types of media, which can be physically active, chemically active, or both physically and chemically active.

As used herein, the term "oil" refers to any lubricant or functional fluid. Non-limiting examples include petroleum-based, semi-synthetic, or synthetic lubricating oils, engine oils, transformer oils, transmission fluids, hydraulic fluids, turbine oils, metal working fluids, and/or edible oils, combinations thereof, and the like. These oils may serve a variety of functions based on their application. Applications include their use in internal combustion engines, vehicle transmissions, hydraulic equipment, electric transformers, turbines (including steam, gas, and industrial turbines), metal working (including machining, grinding, and milling), and rotating equipment. In the presence of oxygen or nitrogen from the air, sulfur from fuel, and/or organics, oxidation may occur. This results in acids or other polar species that may adversely affect the performance of the oil (or its properties) or additives (or their properties) contained in the oil.

For example, transformer fluid is typically a refined mineral oil or biologically derived oil that is stable at high temperatures and has excellent electrical insulating properties. It is used in oil-filled transformers, certain high voltage capacitors, fluorescent lamp ballasts, and some types of high voltage switches and circuit breakers, and the like. Its functions include insulating, suppressing corona and arcing, and serving as a coolant.

Oxidation of the transformer oil can create harmful by-products such as acids and sludge. Acids promote corrosion and catalyze oxidation reactions. They also attack cellulose and accelerate insulation degradation. Sludge precipitates inside the transformer and prevents efficient heat transfer. Due to the particularly deleterious effects of acids, transformer oil must remain essentially acid free over an extended period. Sludging begins when the acid number reaches a certain known level. As a consequence, acid number of the oil is monitored, and oils are typically reclaimed when the acid number reaches about half the sludging value.

In another example, Metal Working Fluids (MWFs) improve product quality in industrial machining and grinding operations. MWFs range from petroleum oils to synthetic fluids and may include emulsifiers, anti-weld agents, corrosion inhibitors, extreme pressure additives, buffers (alkaline reserve), biocides, and other additives. MWFs reduce the heat and friction between the cutting tool and the workpiece, and help prevent burning and smoking. Applying MWFs also helps improve the quality of the workpiece by continuously removing the fines, chips, and swarfs from the tool being used and the surface of the workpiece. Oxidation of the MWFs can create harmful by-products such as acids that promote corrosion and catalyze oxidation reactions. Accelerated oxidation creates sludge and varnish which adversely impacts equipment reliability.

In a third example, turbine oils lubricate and cool turbine bearings. Long-term stress on these oils by heat, aeration, and metal catalysts prematurely degrade the fluid via oxidation and results in organic acids, sludge, coke, and varnish. The acids catalyze oxidation. By-products of oil degradation are often sticky or resinous and can cause a host of problems including servo-valve malfunction, buildup on spool metering edges, restriction of oil flow, reduced spool-to-bore clearances, thermal insulation of the valve, and the loss of stick-slip control. Accordingly, acid sequestration may ameliorate these problems.

In certain embodiments an oil may further comprise a detergent or dispersant. In other embodiments, additives, such as, for example, anti-wear additives, may be present in the oil.

As used herein, the term "structural fiber" refers to fibers that impart structural integrity to the fiber matrix by providing bulk and rigidity to the medium. Typically, the average diameter of such structural fibers is at least about ten microns.

As used herein, the term "small diameter fiber" refers to fibers that improve retention of the strong base flocs and/or bridge larger pores to increase efficiency of the filter media. The structural and/or small diameter fibers retain the strong base flocs in the matrix primarily via physical or mechanical entanglement. Small diameter fibers may be derived from a process of fibrillation of larger fibers, from multi-component fibers such as splittable "segmented pie" fibers or "islands-in-the-sea" fibers, from manufacturing methods such as the electrospinning of polymers, or from manufacturing methods such as those used to make fine glass fibers.

Typically, the average diameter of such small diameter fibers is less than about ten microns and preferably less than about one micron.

As used herein, the term "a matrix formed of mechanically-interlocking structural fibers and interstitial spaces" refers to a three-dimensional arrangement of overlapping fibers in space wherein the voids or interstitial spaces provide the locations where strong base particles may be entrapped.

As used herein, the term "sequestering acids from oil, fluids, or fuel" refers to the ability of a strong base to accept and/or retain combustion acids or organic acids previously in the oil, fluids, or fuel as either soluble free acids, or complexed and/or neutralized from/with detergents, dispersants, or other transfer agents.

As used herein, the term "flocculating agent" refers to a high molecular weight material that is capable of bridging three or more particles using substantially physical, as opposed to chemical, adsorption to anchor the bridges. When several such bridged particles join, a three-dimensional porous structure known as a floc is formed.

Preferably, a flocculating agent will adsorb onto many particles. Thus, the higher the molecular weight, the better the flocculent forms a three-dimensional porous structure or floc. Flocculants can be cationic, anionic, nonionic or amphoteric and are greater than 100,000 grams per mole in molecular weight. They are preferably greater than 1,000,000 grams per mole in molecular weight. In some embodiments, they are linear polymeric structures and/or are minimally cross-linked. Exemplary high molecular weight flocculants include polymers of non-ionic polyacrylamide, polyethylene oxide (often used with a water soluble cofactor such as a phenolic resin like Nylofixan P available from Clariant), cationic polyacrylamide copolymers, anionic polyacrylamide copolymers, and cationic starches. Preferred are versions of these polymers wherein the molecular weight is greater than 100,000; more preferred are versions wherein the molecular weight is greater than 500,000; and most preferred are versions wherein the molecular weight is greater than 1,000,000. Additional non-limiting examples of flocculating agents are listed in Table 3 herein below.

Flocculating agents can be effective at low concentrations, especially those with very high molecular weights and linear structure. Typically, they may be used at concentrations of less than 1.5 weight percent of flocculating agent active polymer relative to the amount of strong base present, and preferably at concentrations of less than 0.5 weight percent.

While not wishing to be bound by theory, it is believed that flocculating agents append to a particle through point attachments as opposed to attachment to a portion of the particle surface. As a result, the floc formed by a flocculating agent can be broken by excess agitation, and does not typically reform when the agitation is decreased. This is particularly true when an excess amount of flocculating agent is used. In general, point attachment translates to minimum coverage of a particle's outer surface while only minimally reducing adsorption efficiency.

In the fabrication of filter media, flocculating agents increase the retention efficiency of fine materials during formation. In a strong base filter material, they increase retention efficiency without sacrificing adsorption capacity.

While most flocculating agents are used in aqueous systems, it is contemplated in this invention that flocculating agents can be used in non-aqueous wet-lay filter media fabrication processes, as described in more detail below.

Organic polymer flocculating agents may in some instances be classified as anionic (including co-polymers of acrylamide and acrylate and polyacrylates); cationic (for example, co-polymers of acrylamide and dimethyl-aminoethyl-methacrylate, starch, and/or Mannich amines); non-ionic (such as polyethylene oxide which are sometimes used with a co-factor such as phenolic resins or lignosulfonates), polyacrylamide, and/or polysaccharides); or amphoteric (such as starch). Molecular weights are typically over 1,000,000 and representative examples of commercially available flocculants are listed in Table 3 in the Experimental Section below.

In contrast to flocculating agents, binding agents used to form particle agglomerates are thought to bind to a particle via a more extensive surface attachment. Binding agent attachments are commonly classified as "adhesive" in nature. (See Haberkamp, U.S. Pat. No. 7,250,126 B2, for example). A surface or "adhesive" attachment is stronger than the point attachment of the flocculating agent to a particle. The agglomeration formed with binding agents can not usually be broken by agitation. A process to produce filter media containing strong base particles using a binding agent can be more "robust", i.e. with fewer restrictions on agitation conditions than a process using a flocculating agent. In addition, use of a binding agent typically leads to stiffer and stronger filter media than media formed through use of a flocculating agent.

Liquid adhesive binding agents are typically latexes and are "oil-in-water" emulsions. In contrast, flocculating agents are typically "water-in-oil" emulsions (a.k.a. reverse emulsions), although flocculating agents can also be water soluble powders or liquids.

To further enhance their properties, latex adhesive binding agents are often also cross-linkable. These thermosetting, or heat reactive, polymers are designed to form linkages between polymer chains to form networks that can coat a substantial portion of a particle's surface. This coating can add abrasion and solvent resistance as well as reduce the moisture vapor transmission rate. However, this barrier also reduces the adsorption efficiency of the strong base particle. If cross-linked, adhesive binding agents also form agglomerates that are non-dispersible. In contrast, flocculating agents are not designed to be self cross-linking and do not typically form cross-linked networks.

It is commonly known in the art that processes using flocculating agents require less polymer than do those using binding agents. While not wishing to be bound by theory, it is thought that adsorption of a binding agent via a surface restricts the number of particles to which a given molecule of binding agent can adhere as compared to adsorption to a point (the type of adsorption believed to be the mechanism of action when flocculating agents are employed). The result is that more of a binding agent is required than a flocculating agent to effectively retain the strong base particles. (See Haberkamp, U.S. Pat. No. 7,250,126 B2, for example). A surface attachment, by necessity, covers more surface area than does a point attachment. This results in smaller reactive surface areas for binding agents derived agglomerates that for similarly sized flocs.

As used herein, the term "binder fiber" refers to fibers that bind together structural fibers in the fiber matrix usually through the application of heat and/or pressure. These materials enhance the structural integrity of the fiber matrix and link fibers to one another by melting at an appropriate temperature. One example of such a fiber is UL 410, a polyethylene fiber available from Minifibers, Inc. Sheath-core and other bi- or multi-component binder fibers are also available. These fibers consist of multiple components wherein one part of the fiber, e.g. the core, is made from a material that does not melt (or melts at high temperatures) and another part of the fiber, e.g. the sheath, is made from a material that melts at processing temperatures. An example of one such bicomponent sheath-core fiber is N790 and is available from Kuraray; another is T-201 and is available from Fiber Innovation Technology of Johnson City, Tenn. Geometries other than sheath-core bicomponent fibers are available, and are contemplated within the scope of this invention. In addition to concentric sheath-core, they are made in eccentric and trilobal sheath-core configurations. They are further made in a side-by-side configuration, wherein two dissimilar polymers are formed together such that each polymer has external surface area. Examples include: 50/50 ratio fibers where equal amounts of two polymers comprise a cylindrical fiber, 20/80 ratio fibers wherein dissimilar amounts of two polymers comprise a cylindrical fiber, trilobal fibers wherein one or more of the lobes comprise a polymer unique from the remainder of the fiber, tipped trilobal and cross-shaped fibers wherein the tips of each lobe is of a polymer unique from the reminder of the fiber, and others. These fibers may be added to impart structural integrity to the filter media without substantially reducing adsorption efficiency.

In contrast to flocculating agents, coagulating agents destabilize charged materials by neutralizing the forces that cause them to repel one another rather than bridge particles via chemical or physical adsorption. Coagulating agents counterbalance surface electrical charges and cause the formation of larger masses. They are generally aluminum salts, iron salts, and low-molecular weight "charge neutralizer" polyelectrolytes. The use of coagulating agents is known in the art.

General examples of coagulating agents include compounds such as poly amines, polyquaternaries, poly-diallyldimethylammonium chloride, poly-epichlorohydrin dimethylamine, and/or polyethyleneimines. Molecular weights for linear homopolymers of these materials are typically below 100,000.

As used herein, the term "strong base particle floc" or "strong base floc" refers to three dimensional porous structures that include strong base particles and at least one flocculating agent that is capable of bridging three or more strong base particles using substantially physical rather than chemical adsorption to anchor the bridge.

As used herein, the term "substantially unattached" refers to the relationship between the strong base and the fiber matrix, wherein "substantially" and "substantially all" are as herein defined.

As used herein, the term "physically bound" refers to the manner in which the strong base particles are contained within the fiber matrix, wherein the strong base particles are physically entrapped in the matrix rather than chemically attached to the matrix.

As used herein, the term "intrinsic surface area" refers to the surface area of the strong base materials as received from the supplier.

Fibers useful in making the filter element include but are not limited to: natural fibers such as regenerated cellulose (e.g., rayon), the woolen animal fibers of sheep, goats, alpaca, hog's hair, and the like and other animal related fibers such as silk; woodpulp derived cellulose from trees such as oak, gum, eucalyptus, birch, aspen, beech, redwood, douglas fir, western red cedar, slash pine, loblolly pine, conifers, spruce, fir, cedar, and hemlock, for example; vegetable derived cellulosic fibers from a variety of sources such as abaca, manila hemp, hemp, esparto grass, sisal, jute, kenaf, flax, rice, wheat, rye, sabai, bagasse (sugar cane), bamboo, cannabis, linen, ramie, barley, oat, reed fiber, coconut fiber, cotton, and others; inorganic and mineral fibers including glass, ceramic, silica carbide, asbestos, basalt; and numerous metal fibers like stainless steel, nickel, Fe Cr alloy, nickel alloy, Inconel, Hastelloy, Haynes Alloy, and other of similar ilk; organic synthetic fibers not limited to phenol formaldehyde resins exemplified by resole or novalak resins; poly aramid fibers such as Nomex, Kevlar, or Twaron; polyester fibers like dacron—Poly(ethylene terephthalate) (PET) or poly(butylene terephthalate) (PBT); polyimides such as P84; polyphenylene sulphide (e.g. Ryton); polyurethanes such as Spandex; polytetrafluoroethylene (PTFE), for example, Teflon; polyamides including nylon 6 and nylon 6,6; polyethylenes including high, low, and ultra high density polyethylenes (HDPE, LDPE, UHMWPE); polypropylenes such as Typar or Tekton; polystyrene; polyacrylonitrile such as modacrylic PAN (e.g. Dynel (acrylonitrile and polyvinyl chloride)); and Verel (acrylonitrile and vinylidene chloride); polyvinyl alcohol (PVOH) exemplified by Kuralon; carbon fibers; and fibers comprising polyvinyl chloride (PVC), polyvinyl acetate, acrylics, polyvinylidene chloride, polybenzimidizole (PBI) and the like.

The fibers are, in some embodiments, capable of being fibrillated. Combinations of organic and inorganic fibers and/or whiskers whether fibrillated or not, are contemplated and within the scope of the invention. For example, glass, ceramic, or metal fibers and polymeric fibers may be used together. Glass or metal fibers can provide additional wet strength to the integrated paper.

As used herein, a "micro-particle retention aid system" refers to a micro and/or nano-particle-based chemical additive or mixture of chemical additives that promote fine particle retention efficiency and enhance the formation of a porous solid matrix during filter media fabrication. These systems are characterized by the incorporation of a high molecular weight polymer, preferably of molecular weight greater than 1,000,000, a high level of hydrodynamic shear after introduction of the high molecular weight polymer to strongly disperse the polymer induced flocs, and small, solid, charged micro-particles, and/or micropolymers.

As used herein, the term micropolymer refers to a highly cross-linked water-soluble filamentary micro-network. They are also sometimes referred to solid polymeric micro-spheres or branched anionic water-soluble polymers (BAP). They typically have an ionic surface, a three-dimensional constrained structure, and a sub-micron size. These materials are typically greater than 5 nanometers in diameter and more typically between 30 and 90 nanometers in diameter. They are typically produced by micro-emulsion or dendrimer technology and sometimes used in combination with inorganic microparticles. They are always used as part of a micro-particle retention aid system.

To be more effective, these micro-particles should preferably have either a high specific surface area, for example in the range of about 500 to about 1,200 square meters per grams as in the case of many colloidal silica products or have at least one dimension of the micro-particle that is less than about 5 nanometers, as in the case of solid particles.

Two other characteristics of a micro-particle retention aid system may include an abrupt increase in the rate of water release from the media during the forming and pressing steps, and/or reformation of the flocs even when the fibers/solids have been previously flocced and dispersed using a high molecular weight polymer. Using such a system leads to increased retention, increased porosity, increased drainage, improved formation, dry strength improvements, and increased solids after wet pressing.

The three main types of micro-particles used in a retention aid system are colloidal silica sols or gels, Smectite clays (bentonite, montmorillonite, hectorite), and certain highly cross-linked organic micropolymers that serve a similar function as the solid particles. These micropolymers have been described as "water-soluble filamentary micronetworks." Most commercial micro-particle products have a negative colloidal charge and a high surface area. Various other micro-particles have been reported and include such materials as lignin, alum-based micro-particles, micro-latexes, and treatment of silica colloids with aluminum, boron, or iron. The high molecular weight polymers that have been used in micro-particle systems include cationic starches, guar, cationic acrylamide copolymers, colloidal silica, and anionic acrylamide copolymers, among others.

A micro-particle retention aid system is typically administered by addition of a flocculent agent followed by downstream addition of micro-particles such as colloidal silica, polysilicate micro-gels, bentonite clays, and organic micro-polymers made using micro-emulsion technology. The combined treatment may cause a marked improvement in dewatering. Preferably, sufficient high-molecular weight polymer is also added to induce flocculation. Micro-particles or micropolymers usually are added very late in the approach flow to filter media formation equipment.

While not wishing to be bound by theory, it is believed that the function of the micro-particle or micro-polymer involves release of water from polymer bridges, causing them to contract, and bridging that spans macromolecules adsorbed on different fibers or fine particles. These effects create more streamlined paths for water to flow around the fibers and more open, porous structures in both the floc and the media.

General discussions of flocculating agents and retention aid systems may be found in Kemmer, F. N., Ed. The Nalco Water Handbook, 2nd ed.; McGraw-Hill: New York, N.Y., 1988, ISBN 0-07-045872-3; Moss, N.; Dymond, B.; Flocculation: Theory & Application. Mine and Quarry Journal 1978, May:2; Heitner, H. I., Flocculating Agents, Kirk-Othmer Encyclopedia of Chemical Technology, Wiley: New York, 2004, Vol 11, pp 623-647; Gess, J. M., Ed. Retention of Fines and Fillers During Papermaking, Tappi Press: Atlanta, Ga., 1998, ISBN 0-89852-066-5; and Rodriguez, J. M., Ed. Micro and Nanoparticles in Papermaking, Tappi Press: Atlanta, Ga., 2005. ISBN 1-59510-074-1.

Examples of single component retention systems include NALCO 7191 Plus, a high molecular weight cationic acrylamide copolymer, and Ciba E38, a high molecular weight anionic acrylic acid/acrylamide copolymer. Dual polymer retentions systems are exemplified by the following combinations of commercial products: Kemira Superfloc C-573, a coagulant—low molecular weight polyamide/polyamine polymer formed with epichlorohydrin and dimethyl amine in combination with Ciba E38, a high molecular weight anionic acrylic acid/acrylamide copolymer; and Kemira Superfloc C-573, a coagulant—low molecular weight polyamide/polyamine polymer formed with epichlorohydrin and dimethyl amine in combination with NALCO 7191 Plus, a high molecular weight cationic acrylamide copolymer. Micro particle retention systems are illustrated by the following combinations of commercial materials: Ciba E22S, a high molecular weight cationic acrylamide copolymer in combination with Ciba Particol S1033, a colloidal silica microparticle, 5 nm; and Ciba Telioform M300, an organic crosslinked micro-polymer particle; as well as the combination of Ciba E22S, a high molecular weight cationic acrylamide copolymer with Ciba Hydrocol 2D6, a Bentonite/Smectite Clay, and Ciba Telioform M300, an organic crosslinked micro-polymer particle.

As used herein, the term "biodiesel" refers to a fuel for use in internal combustion engines, especially diesel engines, wherein the organic fuel component or components is derived from a renewable biological resource. Examples include B5, B20, and B100, mixtures of petroleum based diesel fuel and from 5 to 100% fuel of approximately the same boiling point range as the petroleum based fuel that the biodiesel, in part, is replacing in the mixture. The biodiesel replacement fuel is derived from an organic, preferably renewable resource, such as soy, corn, wood product or by-product, grass or other cellulose-based material product.

As used herein, the term "oil containing acids or neutralized acids" refers to an oil that may (1) have free organic acids in solution generated, for example, by oxidation of the organic component or components in the oil in the presence of oxygen or air and an acid catalyst; or (2) have combustion acids and/or oxidation-generated organic acids complexed and or neutralized by at least one of a detergent, dispersant, and/or other transfer additive found in the oil.

As used herein, the term "oxidation of the oil" refers to the propensity of an organic component in the oil, in the presence of oxygen with or without an acid catalyst to replace various carbon-hydrogen bonds with carbon-oxygen bonds. The rate at which this oxidation takes place may be analyzed in any of a number of ways known to one or ordinary skill in the art. For example, the oxidation may be measured by infrared spectroscopy, in particular, FTIR, wherein the increase in the level of certain carbonyl-related absorbances as a function of time may be related to the rate and level of oxidation. (See the ASTM-FTIR procedure, E 2412-04, "Standard Practice for Condition Monitoring of Used Lubricants by Trend Analysis Using Fourier Transform Infrared (FT-IR) Spectrometry", for a more detailed explanation).

As used herein, the term "water-miscible" refers to any solvent that is at least about 50%, preferably at least about 60%, more preferably 70%, yet more preferably 80%, and even more preferably at least about 90% soluble in water. In certain preferred embodiments, the solvent is completely soluble in water.

As used herein, the terms "substantially" and "substantially all" each refer to at least about 60%, preferably 75%, more preferably 85%, still more preferably 95%, with at least about 98% being even more preferred.

Porosity characteristics are discussed throughout the specification. The skilled artisan will readily appreciate that there are a number of methodologies that can be used for assessing porosity characteristics, including gas adsorption and mercury intrusion porosimetry. Gas adsorption is generally capable of measuring virtually all the surface area as defined by a material's internal pores, detecting pores having a diameter of from about 3.5 Angstroms to about 3,000 Angstroms. Among pores in that range, mercury intrusion porosimetry measures a subset of those pores, measuring down to a diameter of about 30 Angstroms. Exemplary mercury intrusion porosimetry equipment and methods are disclosed in "Analytical Methods in Fine Particle Technology," Paul A. Webb and Clyde Orr, Micromeritics Instrument Corporation, Norcross, Ga., Chapter 4, pp 155-191, 1997, and "An Introduction to the Physical Characterization of Materials by Mercury Intrusion Porosimetry with Emphasis on Reduction and Presentation of Experimental Data," Paul A. Webb, pp 1-22, Micromeritics Instrument Corporation, Norcross, Ga., January 2001.

Exemplary Embodiments

Exemplary filter embodiments in accordance with the present invention may be employed within the lubrication system of internal combustion engines to immobilize combustion acids and to control lubricant viscosity. While not wanted to be held to theory, it is believed that combustion acids and soot particles enter the lubricant with combustion blow-by gases and/or through the boundary layer of lubricant that may or may not contain recycled exhaust gas. Soluble weak bases ("dispersants") are typically employed in commercial lubricants to help neutralize combustion acids and to prevent agglomeration of soot particles.

The present invention, in part, provides filter elements for use in chemical filters that employ filtration media comprising a strong base material. The chemical filters can be placed at any location within the lubrication system, such as, for example, the location of a traditional oil filter. The weak bases and combustion acids interact to form acid-weak base complexes (or salts) that travel within the lubricating oil. In certain embodiments, neutralization preferably occurs before the acids reach metal surfaces to produce corrosion and/or before the soot particles form a three dimensional, viscosity-increasing structure. The strong base material in the chemical filter displaces the weak base from the combustion acid-weak base complex. Once the weak base has been displaced from the soluble neutral salts, the combustion acid-strong base salts thus formed will be to a large degree immobilized as heterogeneous deposits with the strong base or with the strong base on a substrate if one is used. Thus, combustion acid salts or complexes that would normally form in the piston ring zone and remain in the lubricant are now removed from the oil and are sequestered in the chemical oil filter. The displaced, regenerated weak base material is effectively recycled to neutralize subsequently produced acids. FIG. 1 is a schematic of the above-described process. In certain instances, transfer of combustion acids from detergents to strong base material not only sequesters the acids and allows recycle of detergents in the lubricant, but may modulate piston deposit formation by reducing the level of these polar salts and/or acid-base complexes from the circulating lubricant.

In certain embodiments, the use of the present filter elements may lengthen the time between oil drains by facilitating the regeneration of weak base additives, reducing lubricant ash content, and/or by slowing the rate of oxidation. The recycling of dispersant weak base materials for reuse in neutralization of the acidic surface of soot can also minimize the increase of viscosity due to soot agglomeration in certain instances. In other embodiments, the chemical filter may decrease piston deposits and reduce corrosion by, for example, transferring combustion acids from combustion acid-weak base complexes in the oil and immobilizing them with strong base in the filter element.

Any fully formulated lubricant containing detergents and dispersants will work well with the chemical filters described by this invention. The lubricating (or crankcase) oil circulating within the lubrication system of a typical internal combustion engine will comprise a major amount of a lubricating oil basestock (or base oil) and a minor amount of one or more additives. The lubricating oil basestock can be derived from natural lubricating oils, synthetic lubricating oils, or mixtures thereof.

Figure 2:
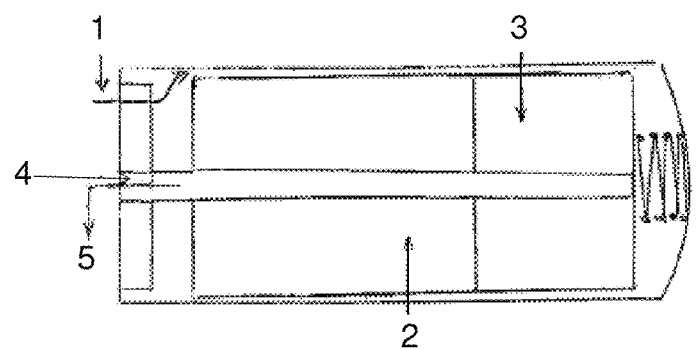
FIG. 2 represents a flow-through schematic of an exemplary oil filter containing a strong base filter element.

As shown in FIG. 2, an exemplary chemical filter is created in the form of a modified conventional oil filter. Lubricant containing dispersant:acid complex enters the filter at entry port 1. The lubricant flows between the exterior wall of the filter and the full flow filter 2 and bypass strong base filter 3. The lubricant then flows radially inward through either filter element 2 or 3. Filter element 2 is a full-flow filter and may or may not contain strong base. Filter element 3 is a by-pass filter and does contain strong base. Either filter element 2 or 3 may be in the form of fluted natural or synthetic filter media or may be of some other construction, such as a stacked disc or wall-flow. The lubricant, having transferred a large portion of acid from the dispersant:acid complex to the strong base, exits with rejuvenated dispersant at 4 and returns to the engine at 5. The dispersant is then available to neutralize more combustion acid and repeat the process.

The features of the chemical filter of FIG. 2 are exemplary only and are not limiting for purposes of properly construing the appended claims. Furthermore, the chemically active filter element 3 and in some cases the filter elements 2 and 3 are drawn simply to illustrate that the chemically active filter element includes a collection of particulate matter that permits the through flow of oil. Other filter configurations, such as cartridge filters, are contemplated as well. The figure is not intended to represent actual dimensionality of filtration media provided by the present invention. The size and distribution of the particulate matter, and the size and distribution of interstitial pores defined between adjacent particles, will be described in more detail below.

Figure 2A:
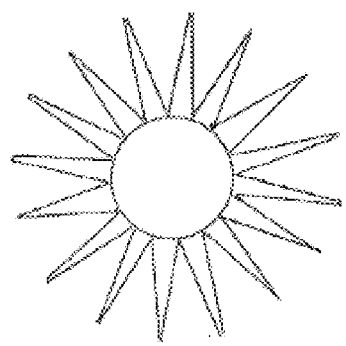
FIG. 2a represents a top-view cross-section of an exemplary pleated filter element that contains strong base flocs described herein.

FIG. 2a depicts a top-view cross-section of a fluted or pleated filter element that contain strong base flocs. This configuration is exemplary only and other filter element configurations, such as stacked disc or wall flow, are contemplated.

Figure 9:
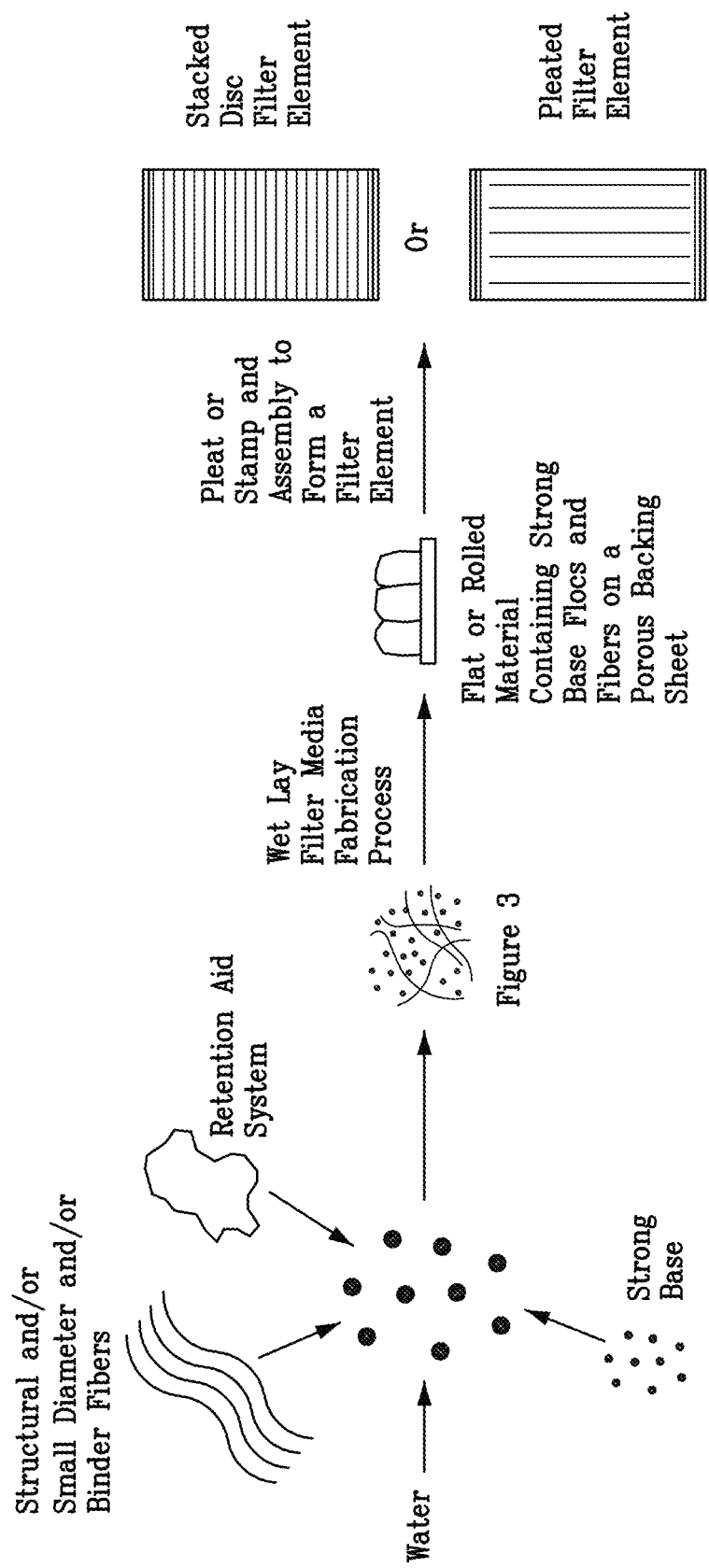
FIG. 9 provides a schematic diagram of an exemplary process to make a strong base filter element used in the oil filter described in FIG. 2.

FIG. 9 depicts an exemplary process by which a strong base filter element described herein may be formed. The process entails forming two separate slurries. The first slurry contains strong base particles suspended in water that is then flocced using a retention aid system which comprises a high molecular weight flocculating agent and optionally micro-particles. Separately, a second slurry is formed containing water, structural fibers, and/or small diameter fibers, and/or binder fibers, or some combination thereof. The two slurries are combined and formed using a wet-lay filter media fabrication process. One example of such a process entails using a commercial Fourdrinier paper machine. The resulting flat or rolled sheet material contains strong base flocs and fibers on a porous backing sheet. This sheet is then stamped or pleated and then assembled to form a filter element using methods known to those skilled in the art. Two examples of a filter element formed from such a process comprise either pleated or stacked disc filter elements.

The strong base material used in the formation of a strong base filter element such as that depicted in FIG. 2 is generally an amorphous material, as received from the manufacturer, but in some embodiments, may be of a more crystalline nature. The strong base particles may be quite small, with particle diameters averaging 1 micron or less, or of an intermediate size, ranging from 3 to 8 microns, or may be larger. The strong base particles of intermediate size may be compressed agglomerations of smaller particles, e.g. smaller particles with diameters of 1 micron average size or less. In order to immobilize the strong base in the filter it is desirable to agglomerate the particles to a larger agglomerate size, e.g. at least about 10, preferably at least about 20, with at least about 30 microns diameter or larger being even more preferred. In maintaining the capacity of strong base particles to accept the transfer of acid from the dispersant:acid complex, it is important to maintain the surface area of the strong base particles to the highest degree possible during any manipulations to agglomerate the particles. Binders are commonly used in the prior art to agglomerate particles. However, binders not only form agglomerates by binding small particles together to form large agglomerates but also bind the agglomerates to the fibers that form the structural matrix of the filter element. By binding the agglomerates to the fibers, the agglomerates are immobilized in the filter. Applicants have found that the use of binding agents can markedly decrease the capacity of the strong base to accept acid from the dispersant:acid complex. While not wishing to be bound by theory, it is believed that the binding agent performs its binding function by attaching itself to the surface of several particles and thus holding them together in a single agglomerate. In attaching the binder to the small particles, particle pores are covered and in this way surface area may be markedly reduced. Applicants have surprisingly found that the use of flocculating agents instead of binding agents leads to the formation of agglomerates of desired size without markedly reducing the capacity of the strong base to accept acid from the dispersant:acid complex. As flocculating agents do not generally attach agglomerates to structural fibers, it is necessary to find another method to immobilize strong base agglomerates in a filter element when flocculating agents are used in place of binding agents.

Figure 3:
FIG. 3 is a scanning electron microscope image (SEM) showing structural and small diameter fibers physically restraining strong base flocs in a chemically active filter medium.

One such method of strong base immobilization comprises the use of small diameter fibers in the filter element. While the attachment of agglomerates to structural fibers, as with a binding agent, can be seen as a chemical immobilization of the agglomerates in the fiber matrix, the entrapment of agglomerates in the filter matrix, such as with flocs and/or small diameter (e.g. fibrillated) fibers, is a physical entrapment. FIG. 3 is a scanning electron micrograph (SEM) of a chemically active filter element embodied within the invention using a flocculating agent plus fibrillated fibers, but without a binding agent. The SEM includes large structural fibers, flocculated small strong base particles and small diameter fibrillated fibers physically immobilizing strong base flocs. Table 4 (found in the Experimental Section below) compares the abilities of a flocculating agent and a latex binding agent to 1) immobilize a strong base (MagChem 50) in a filter matrix and 2) remove octanoic acid (OA) from mineral oil at 110 degrees C. In Table 4, the flocculating agent (filter media samples 2 & 3) immobilizes more strong base than does the latex binding agent (filter medium sample 1) and decreases TAN to a greater proportion than expected based on the increase in % loading of MgO. It is believed that this is a fair directional comparison of a binding agent versus a flocculating agent.

The particles may be formed primarily from a strong base material itself. By "strong base" is meant a base that will displace the weak base from the neutral salts and return the weak base to the oil for recirculation to the piston ring zone where the weak base may be reused to neutralize additional acids. Examples of strong bases suitable for immobilization in solid base filters include, but are not limited to, barium oxide (BaO), calcium carbonate ($CaCO_3$), calcium oxide (CaO), calcium hydroxide ($Ca(OH)_2$) magnesium carbonate ($MgCO_3$), magnesium hydroxide ($Mg(OH)_2$), magnesium oxide (MgO), sodium aluminate ($NaAlO_2$), sodium carbonate ($Na_2CO_3$), sodium hydroxide (NaOH), zinc oxide (ZnO), zinc carbonate ($ZnCO_3$) and zinc hydroxide $Zn(OH)_2$ or their mixtures. Magnesium oxide and zinc oxide, or mixtures thereof, are preferred strong base materials.

Figure 4:
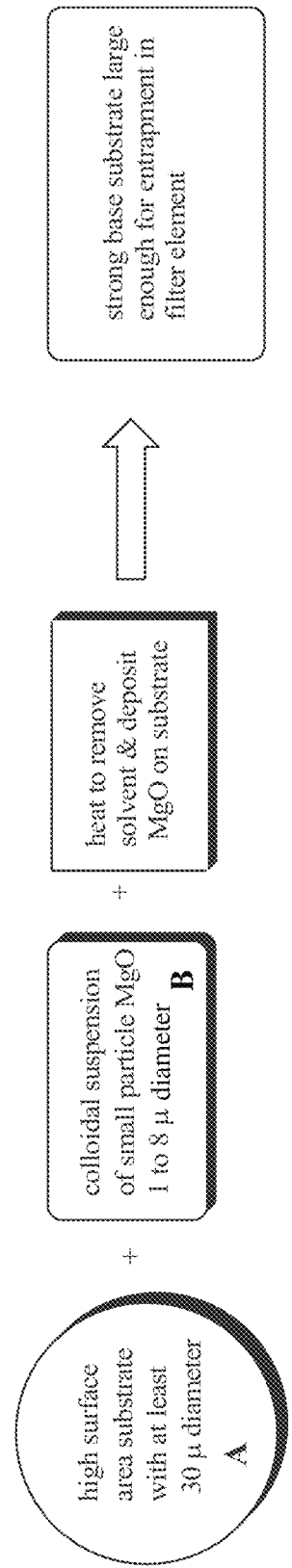
FIG. 4 provides a schematic diagram for deposition of strong base on a substrate

The particles may alternatively be formed from a substrate material onto which a strong base material is disposed. The strong base may be incorporated on or with the substrate by methods known to those skilled in the art. For example, substrate particles can be exposed to a solution of dissolved strong base material and a solvent so that the solution coats the exterior and interior surface areas of the particles. The solvent is then removed, leaving a thin layer of strong base material disposed on the substrate particles. FIG. 4 is a simplified schematic illustrating this process, wherein a substrate particle (A) is coated with a thin layer of a strong base material (B). Suitable substrates include, but are not limited to, activated carbon, carbon black, activated or transition alumina, silica gel, aluminosilicates, layered double hydroxides, micelle templated silicates and aluminosilicates, manganese oxide, mesoporous molecular sieves, MCM-type materials, diatomaceous earth or silicas, green sand, activated magnesite, adsorbent resins, porous clays, montmorillonite, bentonite, magnesium silicate, zirconium oxide, Fuller's earth, cement binder, aerogels, xerogels, cryogels, metal-organic frameworks, isoreticular metal-organic frameworks, and mixtures thereof. Activated carbon has been found to be a preferred substrate on which to deposit a very thin or monolayer of a strong base material. For this purpose it is useful (although not required) that the carbon surface is acidic. In accordance with certain preferred embodiments, having a strong base material "associated" with particulate filtration media includes embodiments where the particles are primarily made from the strong base material itself, as well as embodiments where the strong base material is disposed onto substrate particles (which material itself may or may not contribute to the strong base functionality).

It should be noted that many of the above-listed substrates are physically active materials, and that alternative chemical filter and/or insert embodiments of the present invention may employ mixed filtration media—both chemically and physically active filtration media. For example, a volume of activated carbon can be employed in a chemical filter, and only a portion of the carbon particles be coated with a strong base material. The uncoated carbon particles would serve as physically active filtration media capable of adsorbing any number of oil contaminants, and the coated particles serve as chemically active filtration media capable of immobilizing combustion acids and recycling lubricant dispersants in accordance with the invention. The mixed filtration media can be formed into a single solid structure with binder material. Alternately, the physically active particles could be bound into a first insert or component and the chemically active particles bound into a second insert or component, with the two components assembled within a chemical filter housing.

The amount of strong base material required will vary with the amount of weak base in the oil and the amount of acids formed during engine operation. However, since the strong base material is not being continuously regenerated for reuse as is the weak base material, the amount of strong base material preferably provides a strong base capacity at least equal on an equivalent basis to one fourth of the neutralization capacity of the detergent in the oil, one half, still more preferably an amount equal, with a capacity of at least two or more times the neutralization capacity of the detergent employed in the oil. In cases where the detergent level has been reduced from normal loadings, or the detergent eliminated altogether, the amount of strong base should be at least equal on an equivalent basis to one fourth of the neutralization capacity of a 0.6% ash of detergent level, more preferably at least the neutralization capacity of a detergent level having a 1.2% ash or higher ash.

Accordingly, certain embodiments of the present invention are directed to filter elements for sequestering acids from oil or fuel, comprising:
- a matrix formed of mechanically-interlocking structural fibers and interstitial spaces (as shown, for example, in FIG. 3);
- strong base particles within the matrix for sequestering acids from oil or fuel, the strong base particles having an average particle size less than the average cross-section of the interstitial spaces; and
- a high molecular weight flocculating agent to retain a strong base particle floc formed within the matrix;
wherein:
  1) the smallest unit dimension of the strong base particle floc formed is greater than the average cross-section of the interstitial spaces;
  2) the strong base particles are substantially unattached to the mechanically-interlocked fibers and are physically bound within the matrix;
  3) there is substantially no latex chemically binding the strong base particles to the matrix; and
  4) the strong base particles constitute at least 30% by weight of the filter element.

Preferably, the flocculating agent has a molecular weight of at least about 100,000, more preferably at least about 500,000, with at least about 1,000,000 being even more preferred.

In other preferred embodiments of the filter elements, the matrix further comprises at least one second mechanically-interlocking fiber selected from fibrillated structural fibers or structural fiber portions, and fibrillated or non-fibrillated small diameter fibers or small diameter fiber portions; or any combination thereof; wherein the total amount of the at least one second fiber is less than about 10%, preferably less than about 5%, more preferably less than about 2% by weight of the total amount of structural fiber present in the filter element.

In still other embodiments of the filter elements, the matrix further comprises at least one fiber to improve efficiency of filtration of particulates, for example, such as glass fibers. These added fibers may gather preferentially in the interstitial spaces of the filter matrix and assist in the entrapment of particulates in the oil or fuel. Preferably, these fibers are glass, more preferably of less than about 1 micron in diameter. Still more preferably, they do not substantially reduce throughput through the filter matrix. In some embodiments, the total amount of the improved filtration efficiency fiber is less than about 10%, preferably less than about 5%, more preferably less than about 2% by weight of the total media in the filter element.

In still other embodiments of the filter elements, the matrix further comprises at least one type of fiber to improve bulk or loft of the filter media and to improve porosity, for example, such as polyester fibers or high bulk pulps. The high bulk pulps are typically of very high purity and often contain more than 90% alpha-cellulose content. Examples of such fibers include cotton linters (available from Buckeye Technologies of Memphis, Tenn. as Cotton Linter Pulp Grade 512) or mercerized kraft pulps (available as HPZ or HPZ-III from Buckeye Technologies of Memphis, Tenn. or Porosanier-J-HP from Rayonier Performance Fibers of Jacksonville, Fla.). The polyester fibers (available from Minifibers, Inc of Johnson City, Tenn.) are relatively stiff and improve porosity of the filter media as well. A preferred embodiment is short-cut polyethylene terephthalate (PET) fiber in 6 or 12 millimeter lengths and in 3 to 15 denier per filament. PET fibers with a diameter of about 60 microns are more preferred. In some embodiments, the total amount of the improved porosity fiber is less than about 10% and preferably less than about 5% by weight of the total media in the filter element.

In certain other preferred embodiments, the average particle size of the strong base particles is less than about 10 microns.

In some embodiments, the strong base particles preferably comprise magnesium hydroxide, magnesium oxide, zinc oxide, or a combination thereof; more preferably magnesium oxide or zinc oxide, or a combination thereof; with magnesium oxide being even more preferred.

In certain other embodiments, the strong-base-particle-containing filter medium in the filter element has a total acid sequestration capacity of at least about 13 millimoles of octanoic acid per mole of magnesium oxide or zinc oxide or combination thereof as measured by the Static Test (see Experimental Section below).

The invention also embodies aspects wherein the strong base particles after incorporation into the filter element retain at least 40% of their intrinsic surface area, preferably at least about 50%, more preferably at least about 60%, with at least about 75% being even more preferred, as measured by Hg intrusion porosimetry. As used herein "intrinsic surface area" refers to the surface area that the strong base has as provided by the manufacturer. In certain preferred embodiments the strong base contained in the filter element has a surface area of at least 2000 m$^2$ as measured by Hg intrusion porosimetry; more preferably at least 3500 m$^2$ and still more preferably at least 5000 m$^2$ as measured by Hg intrusion porosimetry.

In some preferred embodiments, the strong base contained in the filter element constitutes at least about 40% by weight of the filter element; more preferably at least about 50%; still more preferably at least about 60%, yet more preferably at least about 70%, with at least about 80% being even more preferred, wherein the backing or other sheet, if present in the filter element, is excluded from the percent weight calculation.

A wide range of fibers may be used as structural fibers, small diameter fibers, or both, in the present invention. In certain embodiments, the structural fibers of the filter element comprise cellulosic fibers, wood fibers, glass fibers, or synthetic fibers, or a combination thereof. In embodiments wherein synthetic fibers are employed in whole or in part, the synthetic fibers comprise at least one of polyester, polynitrile, including for example polyacrylonitrile, and polyolefin fibers, or a combination thereof. In some embodiments, at least some of the structural fibers are partially fibrillated.

In certain aspects the structural or small diameter mechanically-interlocking fibrillated fibers or fibrillated fiber portions comprise polyacrylonitrile or lyocell-type cellulosic fibers.

In other embodiments, the structural fibers preferably have diameters in the range of about 1 to about 60 microns in diameter, preferably about 10 to about 60 microns in diameter. In certain alternative embodiments, the structural fibers preferably have diameters in the range of about 1 to about 50 microns in diameter, and preferably about 10 to about 50 microns in diameter.

In still other embodiments, the small diameter fibers or small diameter portions average in the range of about 10 nanometers to about 10 microns in diameter, preferably have diameters in the range of from about 0.05 microns to about 10 microns in diameter, more preferably from about 0.05 microns to about 5 microns. In other preferred embodiments, the small diameter fibers or small diameter portions have diameters in the range of from about 0.1 microns to about 2 microns. In certain aspects of the invention, at least some of the small diameter fibers or fiber portions are formed by a process of fibrillation of larger diameter fibers. In certain other preferred embodiments, the small diameter fibers or fiber portions are made from low melt polyethylene, polyaramid, or polyvinyl alcohol. In still other preferred embodiments, the small diameter fibers or fiber portions are made from glass. In still other preferred embodiments, the small diameter fibers may be derived from multi-component fibers such as splittable "segmented pie" fibers or "islands-in-the-sea" fibers, from manufacturing methods such as the electrospinning of polymers, or from manufacturing methods such as those used to make fine glass fibers.

In certain embodiments, high molecular weight flocculating agents are employed to form a strong base particle floc substantially retained within the matrix. As used herein, the term substantially retained means at least about 50, 60, 70, 80, 90, or even at least about 95% retention of the material being retained.

In certain preferred embodiments, the flocculating agent is present in the filter element at a level of less than about 2% by weight of total solids, preferably less than about 1.5% by weight; with a level of less than about 0.5% by weight of total solids being even more preferred.

In certain aspects of the invention, the flocculating agent comprises a polyacrylamide or a co-polymer thereof; in other aspects, it comprises polyethylene oxide.

In some embodiments it is beneficial to add a further micro-particle or nano-particle retention aid. Preferably the micro-particle or nano-particle retention aid comprises at least one of colloidal silica, a smectite clay mineral, and an organic micro-polymer.

In certain embodiments, the strong base floc utilized to retain the strong base particles within the matrix comprises:
strong base particles containing magnesium oxide or zinc oxide or combination thereof and having an average particle size of about 0.1 to about 10 microns; and
a high molecular weight flocculating agent;

wherein:
the floc formed from contacting of the flocculating agent and the strong base particles has an average cross-section distance of greater than about 10 microns;
the strong base particles in the floc retain at least about 40% of their intrinsic surface area as measured by a Hg intrusion porosimetry.

In certain preferred embodiments, the strong base particles in the floc comprise magnesium carbonate, magnesium hydroxide, magnesium oxide, zinc oxide, or a combination thereof; more preferably magnesium oxide.

In some preferred embodiments, the high molecular weight flocculating agent has a concentration of less than about 1.5% by weight of the strong base particles in the floc.

In other preferred embodiments the floc further comprises a micro-particle or nano-particle retention aid. In certain more preferred embodiments, retention aid comprises at least one of colloidal silica, a smectite clay mineral, and an organic micro-polymer.

Numerous organic fluids may be treated or contacted by the filter elements of the present invention, including oils and/or fuels. For example, the oils to be filtered may include lubricating oils, a transformer oils, a transmission fluids, a hydraulic fluids, or edible oils. In other aspects fuels such as biodiesel may be contacted or treated with the filter elements of the present invention.

In certain aspects of the invention, filtration of the biodiesel fuel through the filter element reduces the total acid number (TAN) to at least about 0.8, preferably at least about 0.5, more preferably at least about 0.3, still more preferably at least about 0.15, as measured by ASTM method D664. For certain practical biodiesel applications, reductions to at least about 0.5 are preferred.

In certain embodiments, it is useful to further strengthen the strong base in the filter element by adding a porous backing sheet material, preferably a backing sheet having a dry tensile strength of at least about 5 pounds per inch as measured by ASTM method D828. Examples of such materials are available from Fiberweb, Inc. of Old Hickory, Tenn. under the name of Reemay.

The invention also includes methods of use for the disclosed filter elements. For example, the invention includes methods for preparing a filter element for sequestering acids or neutralized acids in at least one oil, such as that depicted in FIG. 9, comprising:
slurrying strong base particles in water, water-miscible solvent, or a combination thereof;
adding a high molecular weight flocculating agent to floc the strong base particles;
adding structural fibers, or structural fiber portions, or small diameter fibers, or small diameter fiber portions, or any combination thereof, to the slurry to form a fiber matrix interspersed with the floc of strong base particles;
contacting the fiber matrix with a backing sheet material;
substantially removing the water, water-miscible solvent, or combination thereof; and
depositing the fiber matrix onto the backing sheet material.

Other methods of the present invention are useful for sequestering acids from oil containing acids or neutralized acids originating in the combustion and lubrication system of an internal combustion engine, or for sequestering acid from oil containing acids or neutralized acids in an oil circulation system, the methods comprising:
contacting in a lubricating oil circulation system a filter element with a lubricating oil containing acids or neutralized acids, or a mixture thereof, wherein the filter element comprises:
- a matrix formed of mechanically-interlocking structural fibers and interstitial spaces;
- strong base particles within the matrix for sequestering acids from the oil, the strong base particles having an average particle size less than the average cross-section of the interstitial spaces; and
- a high molecular weight flocculating agent to retain the strong base particle floc formed within the matrix;

wherein:
1) the smallest unit dimension of the strong base particle floc formed is greater than the average cross-section of the interstitial spaces;
2) the strong base particles are substantially unattached to the mechanically-interlocked fibers and are physically bound within the matrix;
3) there is substantially no latex chemically binding the base particles to the matrix; and
4) the strong base constitutes at least 30% by weight of the filter element;

the filter element causing at least a portion of the acids to remain with the strong base particles within the filter element; and wherein the strong base particles have a total surface area, as measured by Hg intrusion porosimetry, of at least 10 $m^2$/gram.

Other methods use a similar filter element to that described immediately above for reducing oxidation of an oil, comprising:
- contacting the oil with a filter element to sequester acids at a rate such that oxidation of the oil is decreased by at least about 20% relative to the rate of oxidation in an oil in contact with a non-base containing filter element.

The strong base flocs are formed with smallest unit dimensions greater than the average cross-section of the interstitial spaces to promote their retention in the filter element matrix. Rather than binding agents such as latexes that tend to coat particle surfaces and reduce available particle surface area, flocculating agents are used to floc the strong base particles in order to maximize the surface area of the strong base particles useful for the sequestration of acids in the oil. In the substantial absence of binding agents that typically lend strength to filter matrix at the expense of neutralization/sequestration capacity, the invention preferably utilizes a porous backing sheet, scrim, or other support thereby maximizing the ability of the filter element of the invention to sequester and/or neutralize acids in oil or fuel. In order to achieve the sequestration capacity desired in the invention, strong base particles will preferably have a total surface area, as measured by Hg intrusion porosimetry, of at least 10 $m^2$/gram.

In general, the methods of the invention employ in various preferred embodiments, at least one of the preferable filter element embodiments. For example, in some preferred embodiments, the methods employ strong base particles within the filter element comprising magnesium oxide.

In other preferred embodiments, the filter element porous backing sheet material has a dry tensile strength of at least about 5 pounds per inch as measured using ASTM method D828.

Experimental Section

Static Test for Acid Removal Procedure (Measurement of Total Acid Number (TAN)

A known mass of mineral oil (Alfa Aesar—A Johnson Matthey Company, 30 Bond Street, Ward Hill, Mass., 01835, USA, 800-343-0660, CAS 8020-83-5) was weighed into a beaker. Enough octanoic acid (98%, Alfa Aesar—A Johnson Matthey Company, Shore Road, Port of Heysham Industrial Park, Heysham, Lancashire, LA3 2XY ENGLAND, CAS 124-07-2) to bring the Total Acid Number (TAN, as measured by ASTM D-664) of the resulting solution to its target value was then weighed into the same beaker. The solution was then thoroughly stirred to give a uniform solution.

A total of 90.0 grams of this stock solution was then weighed into to a four ounce glass jar. A single piece of pre-weighed filter media was added and the jar was sealed with an aluminum lined lid. A blank solution containing no media was also prepared. The jars were then shaken to ensure that the media was thoroughly saturated and the solution was well mixed. The jars were then placed into a shallow tray and put into a forced air oven (Model 1305U, VWR International, Sheldon Manufacturing, 300 N $26^{th}$ Avenue, Cornelius, Oreg., 97113, USA) that was pre-heated to 110 degrees Celsius. The tray containing the jars was then removed and shaken briefly every 30 minutes to mix the solution.

After fours hours (or other time, as noted) in the oven, the jars were removed. A volume of 60 mL was decanted from each jar and placed into a centrifuge (International Clinical Centrifuge, Centrifuge Model CL, International Equipment Company, 300 2nd Avenue, Needham, Mass. (MA), 02494, USA). The solution was spun at approximately 3200 rpm for 5 minutes after which the solution was decanted into a clean sample vial. The solution is then analyzed for Total Acid Number as specified in ASTM D 664-06 (Standard Test Method for Acid Number of Petroleum Products by Potentiometric Titration).

Table 3 provides a non-limiting list of commercially available flocculents and micro-particles that, among others, may be useful in certain aspects of the present invention. These flocculents are useful for the preparation of flocs that may comprise the filter elements of the invention. The filter elements of the invention may be subsequently fluted or otherwise shaped or transformed into shapes that are compatible with chemical oil filters.

TABLE 3

Commercially Available Flocculents and Micro-particles

| Product Name | Manufacturer | Chemical Type | Description |
|---|---|---|---|
| Polymin SK | BASF | Cationic/nonionic flocculent | Polyethlyene Imine (PEI) |
| Magnafloc E32 | Ciba Specialty Chemicals | Anionic Flocculent | High molecular weight anionic PAM |
| Magnafloc E38 | Ciba Specialty Chemicals | Anionic Flocculent | High molecular weight anionic PAM |
| Magnafloc E42 | Ciba Specialty Chemicals | Anionic Flocculent | High molecular weight anionic PAM |

TABLE 3-continued

Commercially Available Flocculents and Micro-particles

| Product Name | Manufacturer | Chemical Type | Description |
|---|---|---|---|
| Polyflex X100 | Ciba Specialty Chemicals | Anionic Flocculent | Copolymer of acrylamide and sodium acrylate |
| Particol S1033 | Ciba Specialty Chemicals | Anionic Flocculent | Colloidal Silica |
| Particol CA | Ciba Specialty Chemicals | Anionic Flocculent | Polysilicate Microgel |
| Percol E22S | Ciba Specialty Chemicals | Cationic flocculent | Copolymer of quaternary acrylate salt and acrylamide |
| Percol 3320 | Ciba Specialty Chemicals | Cationic flocculent | Copolymer of quaternary acrylate salt and acrylamide |
| Percol 3232L | Ciba Specialty Chemicals | Cationic flocculent | Copolymer of quaternary acrylate salt and acrylamide |
| Hydrocol 2D6 | Ciba Specialty Chemicals | Micro-particle | Bentonite |
| Hydrocol 2D7 | Ciba Specialty Chemicals | Micro-particle | Bentonite |
| Hydrocol OR | Ciba Specialty Chemicals | Micro-particle | Bentonite |
| Hydrocol WH | Ciba Specialty Chemicals | Micro-particle | Bentonite |
| Telioform M300 | Ciba Specialty Chemicals | Organic/Polymeric Micro-particle | Micropolymer |
| Telioform M305 | Ciba Specialty Chemicals | Organic/Polymeric Micro-particle | Micropolymer |
| Telioform B3015 | Ciba Specialty Chemicals | Organic/Polymeric Micro-particle | Micropolymer |
| Telioform S33 | Ciba Specialty Chemicals | Organic/Polymeric Micro-particle | Micropolymer |
| Telioform B3005 | Ciba Specialty Chemicals | Organic/Polymeric Micro-particle | Micropolymer |
| Polyflex CP3 | Ciba Specialty Chemicals | Organic/Polymeric Micro-particle | Micropolymer |
| Percol 2300 | Ciba Specialty Chemicals | Nonionic flocculent | High molecular weight nonionic PAM |
| UCARFLOC Polymer 304 | Dow Chemical | Nonionic flocculent | Polyethylene Oxide (PEO) |
| UCARFLOC Polymer 309 | Dow Chemical | Nonionic flocculent | Polyethylene Oxide (PEO) |
| R 9855UH | Kemira | Cationic flocculent | Polyacrylamide copolymer |
| R 9820 | Kemira | Cationic flocculent | Polyacrylamide copolymer |
| R 9809 LV | Kemira | Cationic flocculent | Polyacrylamide copolymer |
| R 9802 | Kemira | Cationic flocculent | Polyacrylamide copolymer |
| C 1050 | Kemira | Cationic flocculent | Cationic Polyamine, epicholohydrin |
| Fennofix C 1200 | Kemira | Cationic flocculent | Polyethlyene imine |
| Fennosil 515 | Kemira | Anionic Flocculent | Colloidal silica |
| CORE SHELL 71305 | Nalco | Cationic flocculent | Polyacrylamide copolymer |
| NALCO 7191 PLUS | Nalco | Cationic flocculent | Polyacrylamide copolymer |
| OPTIMER 7193 PLUS | Nalco | Cationic flocculent | Polyacrylamide copolymer |
| OPTIMER 7190 PLUS | Nalco | Cationic flocculent | Polyacrylamide copolymer |
| RediBOND 2038A | National Starch | Amphoteric flocculent | Amphoteric Starch |
| RediBOND 5330AA | National Starch | Cationic flocculent | Cationic Starch |

PAM = polyacrylamide

EXAMPLE 1

Preparation of Filter Media Using a Formette Dynamique Automated Dynamic Handsheet Former Retention Aid Preparation All Retention Aid (RA) materials listed in Tables 1 and 2 were prepared by making 1% by weight solutions in water. To do so, three grams of RA were added to 297 grams of tap water followed by vigorous shaking to ensure the emulsions were properly inverted and/or the solutions were uniformly dispersed. The solutions were aged for a minimum of 30 minutes.

Cellulose Pulp Preparation

The cellulose fibers were dispersed with minimal refining in a Valley Beater to a concentration of 1.5% by weight using high freeness bleached southern softwood Kraft pulp.

Synthetic Polymer Preparation

The fibrillated or glass fibers were added in the amounts specified in Table 1 to two liters of tap water and stirred in a blender (The Herman Manufacturing Company, Lancaster Ohio) and dispersed for two minutes. Polyethylene fiber and 500 milliliters of tap water were then added and stirred for an additional two minutes. This slurry was then added to eight liters of a stirred 1.5% by weight pulp. The combined slurry was then stirred vigorously for a minimum of 5 minutes and where designated in Table 2, a coagulant was added after 5 minutes. The mixture was then vigorously stirred for a minimum of an additional 5 minutes.

TABLE 1

Formulations

| Component | Units | Trial 1 | Trial 2 | Trial 3 | Trial 4 | Trial 5 | Trial 6 |
|---|---|---|---|---|---|---|---|
| Pulp (Softwood Cellulose Fibers) | (Liters of 1.5 weight % pulp) | 8 | 8 | 8 | 8 | 8 | 8 |
| MgO (Martin Marietta Magchem 50) | (grams) | 250 | 250 | 250 | 250 | 250 | 250 |
| PE Fiber (Minifibers UL 410) | (grams) | 30 | 30 | 30 | 30 | 30 | 30 |
| Small Diameter Fibers | | | | | | | |
| Acrylic (Sterling CFF V114-3) | (grams) | 69.5 | | | 69.5 | | |
| Lyocell (EFTec L040-6) | (grams) | | 104.1 | | 104.1 | | |
| Glass (Evanite 710 BDC) | (grams) | | | | | 21.0 | |
| Kevlar (Dupont Merge 1F361) | (grams) | | | | | | 41.7 |
| Retention Aids | | | | | | | |
| Nalco 7191 Plus | (mL of 1 weight % aqueous solution) | 42.0 | | | 42.0 | | |
| Ciba E38 | (mL of 1 weight % aqueous solution) | | | 32.0 | 32.0 | | |
| Kemira Superfloc C-573 | (mL of 1 weight % aqueous solution) | | | 126.0 | 125.0 | | |
| Ciba E22S | (mL of 1 weight % aqueous solution) | | | | | 42.0 | 42.0 |
| Ciba Particol S1033 | (mL of 1 weight % aqueous solution) | | | | | 32.0 | |
| Ciba Hydrocol 2D6 | (mL of 1 weight % aqueous solution) | | | | | | 62.0 |
| Ciba Telioform M300 | (mL of 1 weight % aqueous solution) | | | | | 42.0 | 42.0 |

Table 1a. Acid Removal Capability of Example 1 Filter Medium by the Static Test.

| Sample | TAN* (mg KOH/g oil) | TAN Reduction (%) | TAN Reduction **(Mmol OA/g media) | Media Mass (grams) |
|---|---|---|---|---|
| Control (Oil + Octanoic Acid) | 11.16 | — | | 0 |
| Trial 1 | 6.51 | 41.7 | 13.5 | 0.552 |
| Trial 2 | 6.15 | 44.9 | 15.0 | 0.534 |
| Trials | 6.08 | 45.5 | 16.0 | 0.510 |

NOTES:
Trial 1 caliper was 100 mils
All the rest ranged from 62 to 67 mils
*TAN, total acid number, measured by ASTM D 664 after completion of bottle test, 4 hours @ 110 degrees C.
**Millimoles of octanoic acid removed from solution per gram of filter medium.

TABLE 2

Retention Aid Descriptions

| | Product | Description |
|---|---|---|
| Single Component Retention Systems | | |
| 1 | NALCO 7191 Plus | High molecular weight cationic acrylamide copolymer |
| 2 | Ciba E38 | High molecular weight anionic acrylic acid/acrylamide copolymer |

TABLE 2-continued

Retention Aid Descriptions

| | Product | Description |
|---|---|---|
| Dual Polymer Retention Systems | | |
| 3 | Kemira Superfloc C-573 | Coagulant - Low molecular weight polyamide/polyamine polymer formed with epichlorohydrin and dimethyl amine |
| | Ciba E38 | High molecular weight anionic acrylic acid/acrylamide copolymer |
| 4 | Kemira Superfloc C-573 | Coagulant - Low molecular weight polyamide/polyamine polymer formed with epichlorohydrin and dimethyl amine |
| | NALCO 7191 Plus | High molecular weight cationic acrylamide copolymer |
| Micro-Particle Retention System | | |
| 5 | Ciba E22S | High molecular weight cationic acrylamide copolymer |
| | Ciba Particol S1033 | Colloidal Silica Micro-particle, 5 nm |
| | Ciba Telioform M300 | Organic Crosslinked micro-polymer particle |
| 6 | Ciba E22S | High molecular weight cationic acrylamide copolymer |
| | Ciba Hydrocol 2D6 | Bentonite/Smectite Clay |
| | Ciba Telioform M300 | Organic Crosslinked micro-polymer particle |

MgO Slurry Preparation

Separately, 250 grams of Magchem 50 (Martin Marietta Magnesia Specialties, LLC 2710 Wycliff Road, Raleigh, N.C., 27607) was added to 2 liters of tap water while being stirred. The flocculent(s) were then added slowly and flocculation was observed. This flocked MgO slurry was then slowly added to the fiber slurry and stirred for about 5 additional minutes. The slurry was then further diluted with eight liters of tap water and formed into a sheet as described below.

Sheet Formation

The samples were prepared using a Formette Dynamique Automated Dynamic Handsheet Former (TECHPAP, Inc., 5970 Unity Drive, Suite E, Norcross, Ga., 30071, (770) 734-0442). Prior to formation, the Formette Dynamique drum was lined with a backing sheet of REEMAY 2024 spun-bonded polyester upon which to form the sheet. The instrument was run using a pump pressure of 2 bar to supply pulp to the nozzle and the rotary drum was run at a speed of 900 meters/minute. Once formed, the composite sheet was then blotted and dried.

EXAMPLE 2

Procedure for Preparation of Filter Media Used in Engine Testing

The following procedure was followed to make a sheet measuring about 30×30 cm: Magnesium oxide (Martin Marietta Mag Chem 50), was added to deionized water to form an approximately 0.5% by weight slurry. The slurry was dispersed using a propeller-type laboratory stirrer at low speed. To this mixture, a high molecular weight flocculent such as those described in Table 3 was added at a concentration of about 0.1% by weight of flocculent to magnesium oxide. The magnesium oxide coalesced upon addition of the flocculent. Separately, a slurry containing about 0.3 weight % of cellulose fiber (soft or hard wood pulp) in deionized water was dispersed in a Waring type commercial blender for 40 seconds. A quantity of binder fiber such as polyethylene UL 410 (available from Minifibers, Inc., Johnson City, Tenn.) sufficient to bring the slurry to about 0.31 weight % was added to the slurry and dispersed for an additional 40 seconds. A 30×30 cm sheet of scrim material such as Reemay® 2055 was then placed into the bottom of a hand sheet machine. The fiber containing slurry was then transferred to the headbox of the handsheet machine and diluted by a factor of four. The magnesium oxide slurry was then transferred to the headbox of the handsheet machine and was thoroughly hand-mixed using 8-10 vertical strokes with a mixing paddle. The mixture was gravity drained to form a sheet. Vacuum was used to remove most excess water retained in sheet after its formation. The wet sheet was then placed between blotters and was passed one time between pinch rollers. The sheet was then placed on a drum dryer at 115° C. for 3-4 passes.

A sheet made from the above process resulted in a paper containing about 45% MgO by weight when ashed at 525 degrees Celsius according to ASTM Method D 586 (Standard Test Method for Ash in Pulp, Paper, and Paper Products). The process also resulted in less than 10% loss of MgO in the effluent water based upon mass balance analysis of the water and the paper. Further analysis of sheets made by a process substantially as described above yielded the data shown in Table 4. Table 4 also shows comparative data from a filter element using latex binding agent rather than a flocculating agent to retain the strong base in the filter element matrix.

TABLE 4

Acid Removal Capacity of MgO as a Function of using Flocculating Agent or Binding Agent to Immobilize Base in Paper.

|  | Control | Latex Bound Strong Base Sample 1 | Strong Base Floc Sample 2 | Strong Base Floc Sample 3 |
|---|---|---|---|---|
| % loading MgO* |  | 36 | 41 | 54 |
| TAN** | 7.8 | 4.6 | 3.2 | 1.6 |
| Decrease in TAN Relative to Control |  | 3.2 | 4.6 | 6.2 |

TABLE 4-continued

Acid Removal Capacity of MgO as a Function of using Flocculating Agent or Binding Agent to Immobilize Base in Paper.

|  | Control | Latex Bound Strong Base Sample 1 | Strong Base Floc Sample 2 | Strong Base Floc Sample 3 |
|---|---|---|---|---|
| Amount TAN removed per unit MgO |  | 0.089 | 0.112 | 0.115 |

Control has Mineral Oil + Octanoic acid; Samples 1, 2, and 3 have Mineral Oil + Octanoic acid + MgO; Sample 1 uses a latex binder to anchor the strong base to the matrix, while Samples 2 and 3 use a flocculating agent to agglomerate the MgO within the matrix.
*MgO purchased from Martin Marietta Materials as MagChem 50 % loading measured by D 586 Standard Test Method for Ash in Pulp, paper, and Paper Products
**TAN measured by ASTM D 664 after completion of bottle test, 4 hours @ 110 degrees C.

EXAMPLE 3
Procedure for Flocculation of MgO on Filter Media

Using filtered tap water, 0.5 weight percent solutions/dispersions of the flocculant products shown in Table 5 were prepared. All the solutions were allowed at least 30 minutes for the reverse emulsions to invert properly and shaken vigorously to ensure uniform dispersion. Five grams of Magchem 50 (Martin Marietta) was then weighed out and diluted to 200 grams using filtered tap water. The slurry was then stirred to achieve uniform dispersion.

To this slurry, the amount of 0.5 weight percent flocculant shown in Table 5 was added by weighing it into the container. If multiple components were used, the order of addition is shown in the table. For the microparticle retention aid system, the cationic polyacrylamide was added first, then the slurry was sheared using a Waring-type laboratory propeller blender for 1 minute. The solution of colloidal silica was added followed by the micro-polymer. The flocced solution was then filtered onto a media (Synergex® 6140 available from Fiberweb, Inc.) using a vacuum and dewatered. Before analysis of surface area by Hg intrusion porosimetry, the samples were dried in an oven at 105 degrees Celsius overnight.

TABLE 5

Retention of Intrinsic Surface Area Measured by Hg Intrusion Porosimetry

| Product | Description | Dosage (grams of 0.5% by wt. aqueous solution) | Total Surface Area by Hg Intrusion Porosimetry ($m^2$/gram) | Intrinsic Surface Area Retained (%) |
|---|---|---|---|---|
| NALCO 7191 Plus | High MW Cationic acrylamide copolymer | 1.000 | 32.9 | 44.2 |
| Ciba E38 | High MW Anionic acrylic acid/acrylamide copolymer | 0.400 | 41.8 | 56.1 |
| Dow UCARFLOC 304 + Clariant Nylofixan P | Polyethylene Oxide + Water-soluble phenolic resin | 0.250 2.000 | 33.6 | 45.1 |
| Ciba Percol 2300 | Non-ionic PAM | 0.500 | 46.8 | 62.8 |
| National Starch Redibond 2038A | Amphoteric Starch | 15.000 | 36.3 | 48.7 |
| Ciba E22S + | Cationic polyacrylamide + | 0.400 | 38.4 | 51.5 |
| Ciba Particol S1033 + | Colloidal Silica Microparticle, 5 nm + | 1.500 |  |  |
| Ciba Telioform M300 | Organic Cross-linked micro-polymer | 0.800 |  |  |
| None | None | 0 | 46.8 | 62.8 |
| Magchem 50 | MgO | — | 74.5 | 100 |

PAM = Polyacrylamide
MW = Molecular Weight

EXAMPLE 4

The ability of a strong base filter to sequester combustion acids, maintain the oxidative stability of a lubricant, and/or protect an engine from excessive wear over an extended period of time was evaluated in two engine tests. The Lister Petter TR1 engine was used for both tests. The Lister Petter engine is a single cylinder engine with a maximum power of 5.5 kW and a displacement of 0.773 l. The engine is naturally aspirated with direct fuel injection, has no EGR (exhaust gas recirculation system), and has a sump capacity of 2.4 l of lubricant. Test 1 ran for 318 hours and used the filter recommended by the engine manufacturer. Test 2 ran for 750 hours and used filter medium sample #2 from Table 1 formed into a pleated filter element and inserted into a reusable Parker Racor model LFS 331 reusable filter container with similar filter element dimensions to the filter recommended for a Lister Petter TR1 engine, Lister Petter filter 201-55370. Although the filter dimensions were similar there was slightly less surface area for the filter media from sample #2 than from the recommended Lister Petter filter used in Test 1. Both tests were run at 100% full power, 1800 rpm with 15 ppm S diesel fuel and a SAE 40W1.4% sulfated ash lubricant. The oil consumption in the two tests were similar, 3.61 g/hr for Test 1 and 3.51 g/hr for Test 2, the soot formation rate was similar and the mean oil temperatures and fuel consumption were equal for both tests.

Figure 5:
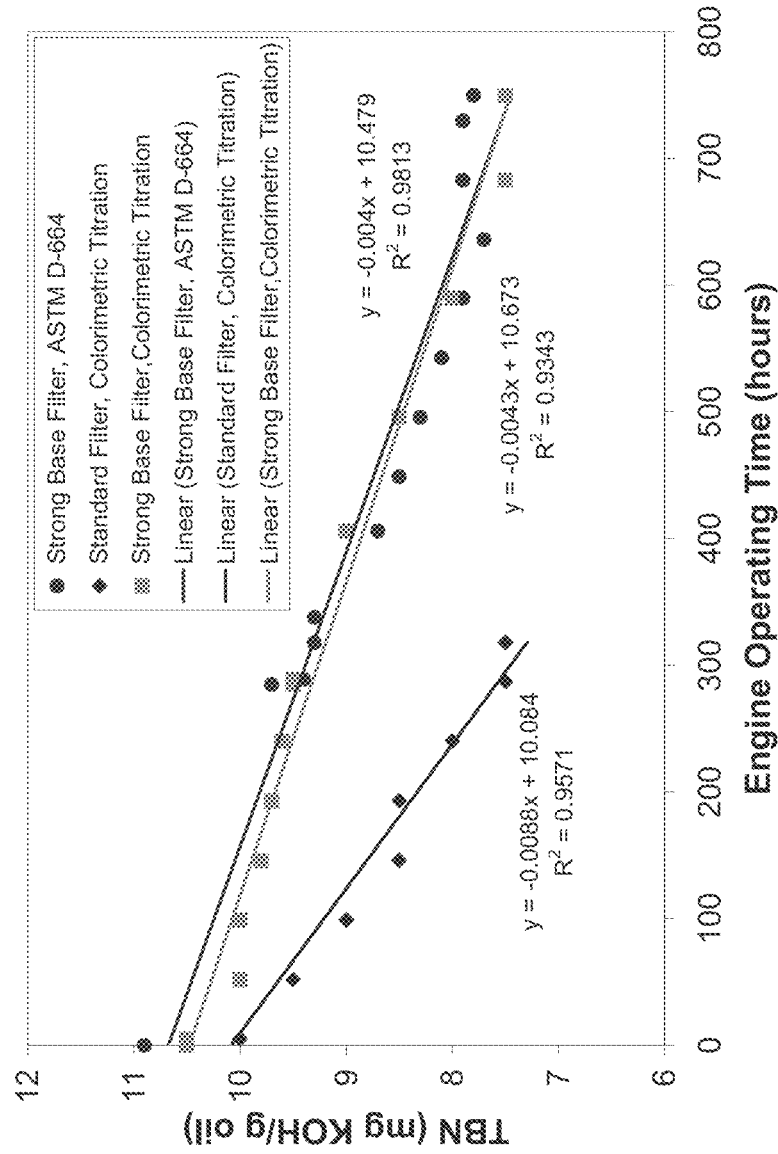
FIG. 5 shows the improved total base number retention in an oil circulation system for an internal combustion engine having a strong base filter versus having a standard filter.

A surprising potency in the strong base filter for sequestering the strong acids that consume detergent is shown in FIG. 5, as measured by the ASTM D-664 TBN Test. The slope for Test 2 using the strong base filter, is one-half that of Test 1, using the filter recommended by the manufacturer. The decrease in slope by one-half for Test 2 versus Test 1 means that half the combustion acid is being sequestered in the strong base filter and half by the detergent in Test 2 vs. all the combustion acid being sequestered by the detergent in Test 1. Since many diesel truck owners change the lubricant when the TBN is cut in half, the implication of this data is that the lubricant change interval can be at least doubled with significant economic and environmental savings.

Figure 6:
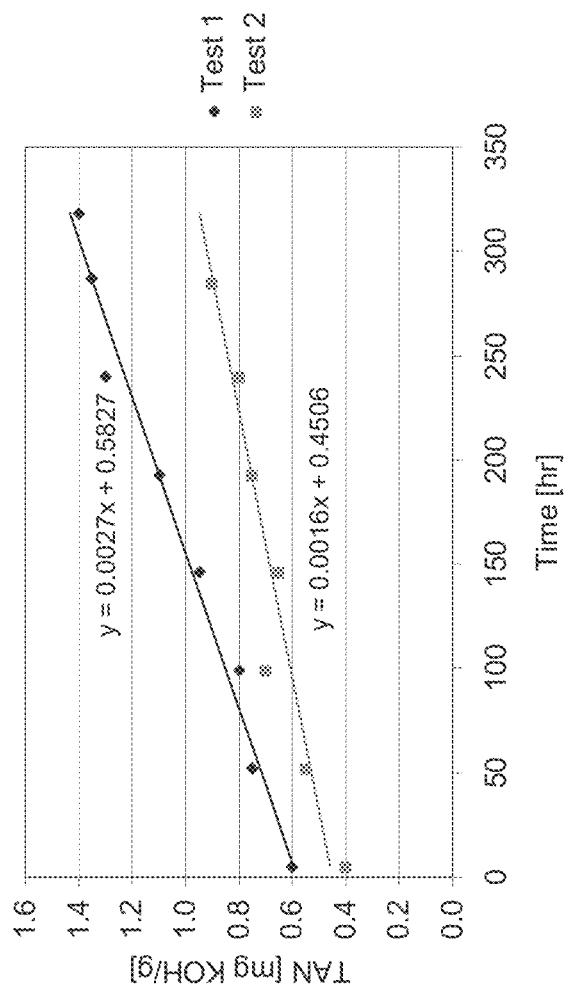
FIG. 6 compares the TAN (total acid number) engine test data for use of a standard filter and a filter element of the present invention.

Current lubrication technology is to a large extent ineffective in neutralizing the weak acids measured by the ASTM D-664 TAN Test. This is obvious when one considers that a fresh lubricant, i.e. a lubricant not yet having been in an engine, has an appreciable TAN even though the lubricant has a full charge of basic additives, i.e., detergent and dispersant. It is the intention of this invention to add to a lubrication system, i.e., considering a chemical oil filter as part of the lubricant system, a capability to neutralize, to at least some extent, the weak acids measured by TAN. The capability of a strong base filter to neutralize weak acids is the result of optimization of the surface area and accessibility of the strong base in the filter as described in the appended claims. The capability of current detergents to neutralize weak acids is degraded by the detergent strong base being buried beneath a surfactant shield. The surfactant shield is necessary to maintain the detergent in the colloidal dispersion and to keep the detergent from separating from the lubricant. Even though it was the intent to add to a oil filter the capability to neutralize weak acids it is surprising the extent of this capability demonstrated in Tests 1 and 2 as shown in FIG. 6. Test 2 with the strong base filter has a markedly lower slope, i.e., slower rate of TAN increase, than does Test 1 with a standard filter. Weak acids can be produced by oxidation of fuel in the combustion chamber and enter the lubricant via blow-by gas or by the oxidation of the lubricant. Neutralization of weak acids is important because unneutralized weak acids may be implicated in the decomposition of anti-wear and anti-oxidant additives. (See for example, "ZnDDP thermal decomposition is acid-catalyzed but not accelerated by the presence of Oxygen". C. E. Legate and H. D. Burnham. Anal. Chem. 32 (1960) 1042). Applicants believed that if a chemical oil filter could lower the rate increase of weak acid formation it would also improve the effectiveness of both the anti-wear and anti-oxidant additives.

Figure 7:
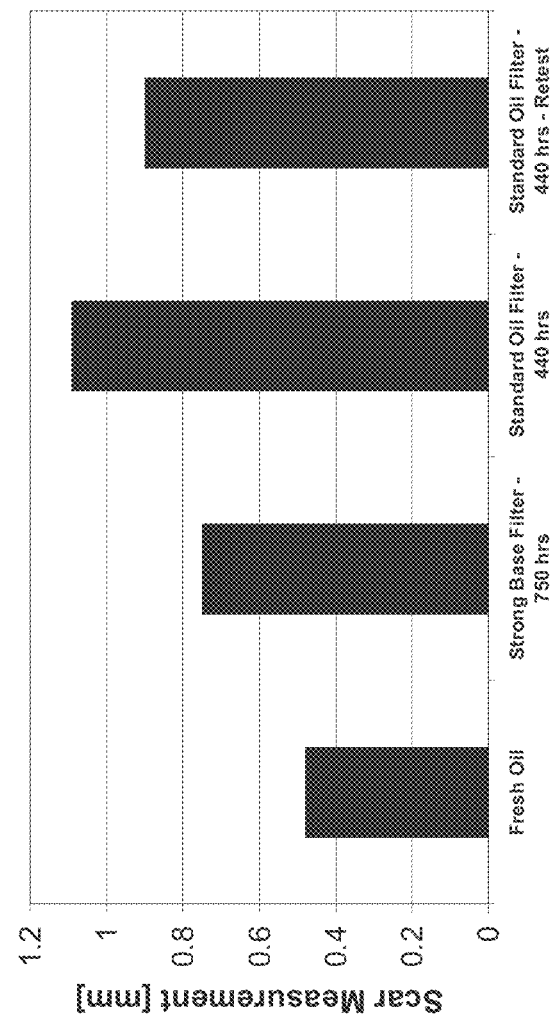
FIG. 7 illustrates improved anti-wear engine performance in the presence of a strong base filter contrasted against a standard oil filter in the Four Ball Wear Test (ASTM D4172 B).
Figure 8:
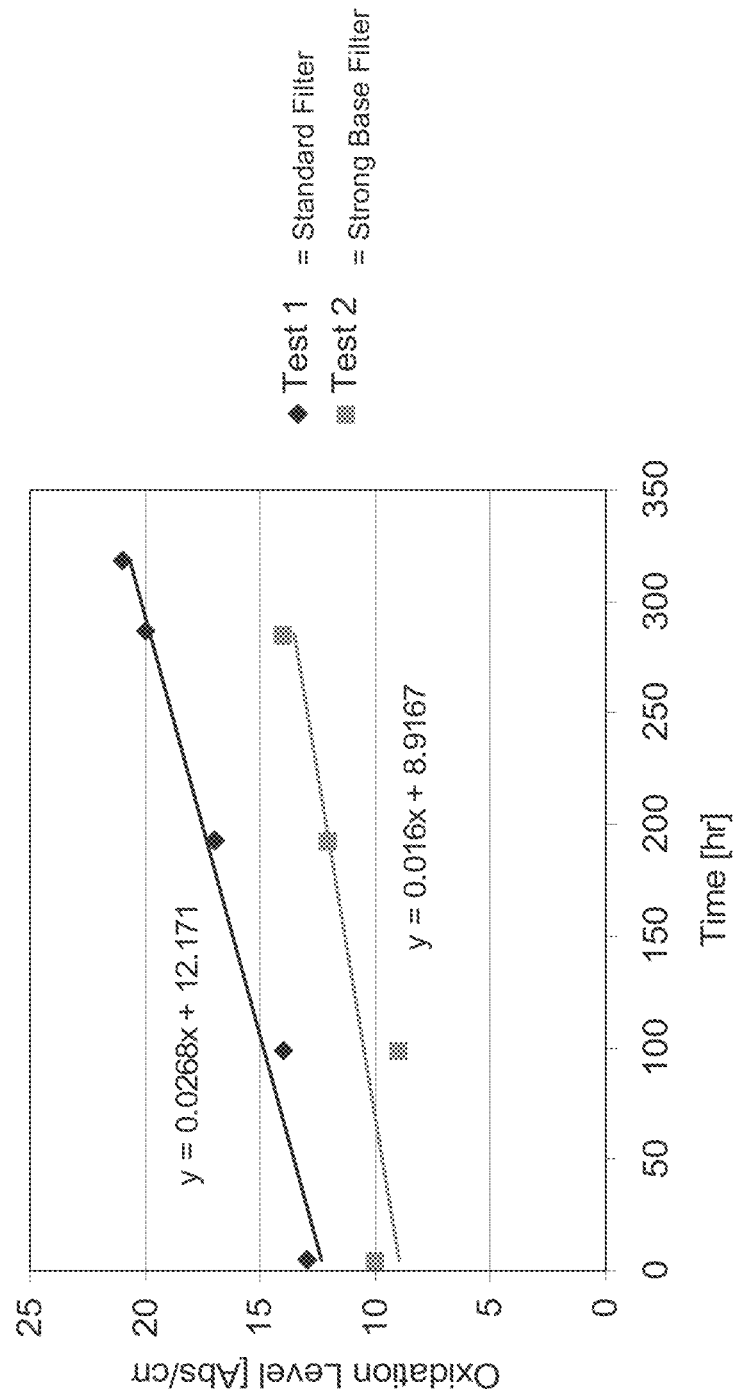
FIG. 8 illustrates the difference in oil oxidation level for an internal combustion engine test comparing use of a standard filter to use of a filter element of the present invention by Fourier Transform Infrared Spectroscopy (FTIR).

FIG. 7 is a comparison of wear, as measured by the ASTM D 4172 B 4-ball wear Test, for Tests 1 & 2. The wear scar for the sump oil from tests using the strong base filter is smaller after 750 hours on test in Test 2 than it is in two tests of the lubricant in Test 1 using the standard filter after 440 hours on test. It can be seen in FIG. 8 that the oxidation level in Test 2 with the strong base filter is lower than in Test 1 with the standard filter. Oxidation level is a measure of the carbonyl adsorption in the infra-red spectrum. The ratio of the increase in TAN in FIG. 6 is very close to the ratio increase of oxidation level in FIG. 8.

The disclosures of each patent, patent application and publication cited or described in this document are hereby incorporated herein by reference, in their entireties.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method for sequestering acids from a lubricating oil containing acids or neutralized acids, or a mixture thereof, originating in the combustion and lubrication system of an internal combustion engine, the method comprising:

contacting in a lubricating oil circulation system a filter element with the lubricating oil containing acids or neutralized acids, or a mixture thereof, wherein the filter element comprises:

a matrix formed of mechanically-interlocking structural fibers and interstitial spaces;

strong base particles within the matrix for sequestering acids or neutralized acids, or a mixture thereof from the lubricating oil, the strong base particles having an average particle size less than the average cross-section of the interstitial spaces; and less than 1.5 wt % of a high molecular weight flocculating agent relative to an amount of the strong base particles, an amount of said flocculating agent sufficient to retain the strong base particles in a strong base particle floc formed within the matrix;

wherein:

1) a smallest unit size dimension of the strong base particle floc is greater than the average cross-section of the interstitial spaces;

2) the strong base particles in the strong base particle floc are substantially unattached to the mechanically-interlocked fibers but are physically bound within the matrix;

3) there is substantially no latex chemically binding the strong base particles to the matrix; and 4) the strong base constitutes at least 30% by weight of the filter element;

wherein the filter element causes at least a portion of the acids or neutralized acids, or a mixture thereof to remain with the strong base particles within the filter element; and wherein the filter element has a total surface area, as measured by Hg intrusion porosimetry, of at least 10 $m^2$/gram.

2. The method of claim 1, wherein the strong base particles within the filter element comprise magnesium oxide.

3. The method of claim 1, wherein the filter element further comprises a porous backing sheet material having a dry tensile strength of at least about 5 pounds per inch as measured ASTM method D828.

4. A method for sequestering acid from a lubricating oil containing acids or neutralized acids, or a mixture thereof, in an oil circulation system, comprising:

contacting the lubricating oil in the oil circulation system with a filter element;

wherein the filter element comprises:

a matrix formed of mechanically-interlocking structural fibers and interstitial spaces;

strong base particles within the matrix for sequestering acids or neutralized acids, or a mixture thereof, from the lubricating oil, the strong base particles having an average particle size less than the average cross-section of the interstitial spaces; and less than 1.5 wt % of a high molecular weight flocculating agent relative to an amount of the strong base particles, an amount of said flocculating agent sufficient to retain the strong base particles in a strong base particle floc formed within the matrix;

wherein:
1) a smallest unit size dimension of the strong base particle floc is greater than the average cross-section of the interstitial spaces;
2) the strong base particles in the strong base particle floc are substantially unattached to the mechanically-interlocked fibers but are physically bound within the matrix;
3) there is substantially no latex chemically binding the strong base particles to the matrix; and
4) the strong base constitutes at least 30% by weight of the filter element;

wherein the filter element causes at least a portion of the acids or neutralized acids, or a mixture thereof, to remain with the strong base particles within the filter element; and wherein the filter element has a total surface area, as measured by Hg intrusion porosimetry, of at least 10 $m^2$/gram.

5. The method of claim 4, wherein the strong base particles within the filter element comprise magnesium oxide.

6. The method of claim 4, wherein the filter element further comprises a porous backing sheet material having a dry tensile strength of at least about 5 pounds per inch as measured ASTM method D828.

* * * * *